(12) United States Patent
Kasahara et al.

(10) Patent No.: US 8,741,279 B2
(45) Date of Patent: *Jun. 3, 2014

(54) GENE DELIVERY SYSTEM AND METHODS OF USE

(75) Inventors: Noriyuki Kasahara, Los Angeles, CA (US); Christopher Reid Logg, Studio City, CA (US); W. French Anderson, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/045,178

(22) Filed: Jan. 11, 2002

(65) Prior Publication Data

US 2002/0127697 A1 Sep. 12, 2002

Related U.S. Application Data

(63) Continuation of application No. 09/409,650, filed on Oct. 1, 1999, now Pat. No. 6,410,313.

(60) Provisional application No. 60/102,933, filed on Oct. 1, 1998.

(51) Int. Cl.
*A61K 48/00* (2006.01)
*C12N 15/00* (2006.01)

(52) U.S. Cl.
USPC ........................................ 424/93.2; 435/320.1

(58) Field of Classification Search
USPC ......... 424/93.2; 514/44; 435/320.1, 91.4, 455
See application file for complete search history.

(56) References Cited

U.S. PATENT DOCUMENTS

| | | | |
|---|---|---|---|
| 5,585,096 A * | 12/1996 | Martuza et al. ............... | 424/93.2 |
| 5,674,486 A * | 10/1997 | Sobol et al. ................ | 424/93.21 |
| 5,770,428 A | 6/1998 | Boris-Lawrie | |
| 5,830,458 A | 11/1998 | Gruber et al. | |
| 5,888,502 A | 3/1999 | Guber et al. | |
| 5,925,345 A | 7/1999 | Blaese et al. | |
| 5,948,675 A | 9/1999 | Klatzmann et al. | |
| 5,997,859 A | 12/1999 | Barber et al. | |
| 6,025,192 A | 2/2000 | Beach et al. | |
| 6,033,902 A * | 3/2000 | Haseltine et al. .......... | 435/320.1 |
| 6,033,905 A | 3/2000 | Eiden et al. | |
| 6,117,681 A | 9/2000 | Salmons et al. | |
| 6,241,982 B1 | 6/2001 | Barber et al. | |
| 6,248,721 B1 | 6/2001 | Chang | |
| 6,303,380 B1 | 10/2001 | Lin et al. | |
| 6,322,969 B1 * | 11/2001 | Stull et al. ....................... | 506/16 |
| 6,410,313 B1 | 6/2002 | Kasahara et al. | |
| 6,410,326 B1 | 6/2002 | Gruber et al. | |
| 6,448,390 B1 | 9/2002 | Albritton et al. | |
| 6,485,965 B1 | 11/2002 | Klatzmann et al. | |
| 6,489,142 B1 | 12/2002 | Torrent et al. | |
| 6,576,463 B1 | 6/2003 | Kasahara et al. | |
| 6,761,884 B1 | 7/2004 | Blaese et al. | |
| 6,806,080 B2 | 10/2004 | Kasahara et al. | |
| 6,899,871 B2 | 5/2005 | Kasahara et al. | |
| 7,056,730 B2 | 6/2006 | Pedersen et al. | |
| 7,211,247 B2 | 5/2007 | Borok et al. | |
| 2002/0042137 A1 | 4/2002 | Richards et al. | |
| 2002/0068362 A1 | 6/2002 | Murray et al. | |
| 2002/0137889 A1 | 9/2002 | Soong et al. | |
| 2003/0003565 A1 | 1/2003 | Dubensky | |
| 2003/0022378 A1 | 1/2003 | Ehrhardt et al. | |
| 2003/0157070 A1 | 8/2003 | Jolly | |
| 2003/0157718 A1 | 8/2003 | Pedersen et al. | |
| 2003/0165466 A1 | 9/2003 | Gromeier et al. | |
| 2003/0219410 A1 | 11/2003 | Calatrava | |
| 2004/0096972 A1 | 5/2004 | Audit et al. | |
| 2004/0142449 A1 | 7/2004 | Tonjes et al. | |
| 2004/0146489 A1 | 7/2004 | Yu et al. | |
| 2004/0197308 A1 | 10/2004 | Takahashi et al. | |
| 2004/0248827 A1 | 12/2004 | Zheng et al. | |
| 2005/0002903 A1 | 1/2005 | Kasahara et al. | |
| 2005/0059004 A1 | 3/2005 | Atabekov et al. | |
| 2006/0084791 A1 | 4/2006 | Pedersen et al. | |
| 2007/0003522 A1 | 1/2007 | Albritton | |
| 2007/0254357 A1 | 11/2007 | Gregory et al. | |
| 2008/0008685 A1 | 1/2008 | Kasahara | |
| 2008/0227736 A1 | 9/2008 | Chen et al. | |

FOREIGN PATENT DOCUMENTS

| | | |
|---|---|---|
| EP | 0 598 029 | 5/1994 |
| EP | 1 059 356 | 12/2000 |
| WO | WO 94/11524 | 5/1994 |
| WO | WO 97/32026 | 9/1997 |
| WO | 9920742 A2 | 4/1999 |

(Continued)

OTHER PUBLICATIONS

Orkin, et al. :Report and Recommendations of the Panel to Assess the NIH Investment in Research on Gene Therapy, www.nih.gov Dec. 1995.*
Verma et al. :Gene Therapy—promises , problems and prospects, Nature vol. 389, Sep. 1997, p. 239-242.*
Miller, et al.: , Targeted vectors for gene therapy, The FASEB Journal, vol. 9, Feb. 1995, p. 190-199.*
Jolly, Douglas : Viral vector systems for gene therapy, Cancer Gene Therapy, vol. 1, 1994, p. 51-64.*
Anderson (Nature, vol. 392, Apr. 25-30, 1998).*
Miller et al. (Human Gene Therapy, vol. 8, pp. 803-815, 1997).*
Vile et al. (Molecular Medicine Today, vol. 4, 2:84-92, 1998).*
Yanez (Gene Therapy, 1998, 5, 149-159).*
Romano (Stem Cells, 2000: 18, 19-39).*

(Continued)

*Primary Examiner* — Ileana Popa
(74) *Attorney, Agent, or Firm* — Joseph R. Baker, Jr.; Gavrilovich, Dodd & Lindsey, LLP

(57) ABSTRACT

A recombinant replication competent retrovirus for gene deliver and gene therapy is provided. The recombinant retrovirus has a heterologous nucleic acid sequence, a sequence encoding a cell- or tissue-specific ligand or a sequence for transcriptional targeting, or a combination of both a cell- or tissue-specific ligand and a cell- or tissue-specific transcriptional targeting sequence.

62 Claims, 16 Drawing Sheets

(56) References Cited

FOREIGN PATENT DOCUMENTS

| | | |
|---|---|---|
| WO | 9936561 A1 | 7/1999 |
| WO | WO 00/18240 | 4/2000 |
| WO | WO 2006/058231 | 6/2006 |
| WO | 2007095201 A2 | 8/2007 |
| WO | 2007107156 A2 | 9/2007 |
| WO | 2008151633 A2 | 12/2008 |
| WO | 2010002937 A1 | 1/2010 |
| WO | 2010036986 A2 | 4/2010 |
| WO | 2010045002 A2 | 4/2010 |

OTHER PUBLICATIONS

Gromeier (ASM News, vol. 68, 2002, p. 438-p. 445).*
Mastrangelo, Seminars in Oncology, 23, 1, 1996, 4-21.*
Tait (Clinical Cancer Res., 5, 1708-1714, 1999).*
Gomez-Navarro, European J. of Cancer, vol. 35, No. 6, pp. 867-885, 1999.*
Meng et al. (Gene Therapy of Cancer, Chapter I, pp. 3-20, 1999).*
Carbone et al., Seminars in Cancer Biology, 2004, 14: 399-405.*
Luqami YA teaches, Med Princ Pract, 2005, 14 Suppl 1: 35-48, Abstract.*
Borisy et al., Proc Natl Acad Sci USA, 2003, 100: 7977-7982.*
El-Aneed et al., European Journal of Pharmacology, 2004, 498: 1-8.*
El-Aneed, Journal of Controlled Release, 2004, 94, 1-14.*
Meyer et al., Review, Cell. Mol. Biol., 2001, 47: 1277-1294.*
Springer et al., J Clin Invest, 2000, 105: 1161-1167.*
Gardlik et al., Review, Med. Sci. Monit., 2005, 11: RA110-121.*
Bestor , J. Clin. Invest., 2000, 105: 409-411.*
Vassaux et al., Expert Opin Biol Ther, 2004, 4: 519-530.*
Miller et al., Human Gene Therapy, vol. 8, pp. 803-815, 1997.*
Vile et al., Molecular Medicine Today, 1998 4 :84-92.*
Anderson, Nature, 1998, 392: 25-30.*
Romano, Stem Cells, 2000: 18, 19-39.*
Meng et al., Gene Therapy of Cancer, Chapter 1, 1999, pp. 3-20.*
Martin, TIBTECH, 1995, 13: 28-35.*
Zlokovic et al., Neurosurgery, 1997, 40: 805-813.*
Lowenstein et al., Review, Current Opinion in Pharmacology, 2004, 4: 91-97.*
Tuszynski, Gene Therapy, 2003, 3: 815-828.*
Fillat et al., Curr Gene Ther, 2003, 3: 13-26.*
over Ram et al., Cancer Research, 1993, 53: 83-88.*
Martuza, Nature Medicine, 1997, 3: 1323.*
Kuryama et al., Int J Cancer, 1997, 71: 470-475.*
Yan et al., Prostrate, 1997, 32: 129-139.*
Kasahara et al., Science, 1994, 266: 1373-1376.*
Murakami et al., Gene, 1997, 202: 23-29.*
Douar et al., Gene Ther, 1996, 3: 789-796, Abstract.*
Vile et al., Virology, 1995, 214: 307-313.*
Coffin et al., Retroviruses, Principle of Retroviral Vector Design, Cold Spring Harbor Laboratory Press, 1997.*
Fig. 1 from Coffin et al.*
Stuhlmann et al., Mol. Cell. Biol., 1989, 9: 100-108.*
Jespersen et al., Gene, 1999, 239: 227-235.*
Cavazzana-Calvo, M., et al. (2000). Gene therapy of human severe combined immunodeficiency (SCID)-X1 disease. Science. 288(5466):669-672.
Murakami, et al., "High-level expression of exogenous genes by replication-competent retrovirus vectors with an internal ribosomal entry site", Gene, vol. 202, pp. 23-29 (1997).
Chang, et al., "Human Immunodeficiency Viruses Containing Heterologous Enhancer/Promoters Are Replication Competent and Exhibit Different Lymphocyte Tropisms", Journal of Virology, vol. 67, No. 3, pp. 743-752, February, 993.
Faustinella, et al., "A New Family of Murine Retroviral Vectors with Extended Multiple Cloning Sites for Gene Insertion", Human Gene Therapy, vol. 5, pp. 307-312, 1994.
Ianni Di M et al., "Retroviral Transfer of Herpes Simplex Virus-Thymidine Kinase and Beta-Galactosidase Genes into U937 Cells with Bicistronic Vector", Leukemia Research, vol. 21, No. 10, 1997 (pp. 951-959.
Schmidt M et al., "Replicating Foamy Virus-Based Vectors Directing High Level Expression of Foreign Genes", Virology, vol. 210, (1995), pp. 167-178.
Terwilliger E F et al., "Construction and Use of a Replication-Competent Human Immunodeficiency Virus HIV-1 that Expresses the Chloramphenicol Acetyltransferase Enzyme," Proceedings of the National Academy of Sciences of the United States, vol. 86, No. 10, 1989, pp. 3857-3861.
Fu et al., "Viral sequences enable efficient and tissue-specific expression of transgenes in Xenopus", Nature Biotechnology, vol. 6, Mar. 1988.
Morgan et al., "Retroviral vectors containing putative internal ribosome entry sites: development of polycistronic gene transfer system and applications to human gene therapy", Nucleic Acid Research, vol. 20, No. 6, pp. 1293-1299.
Jolly, Viral vector systems for gene therapy. Cancer Gene Therapy 1:51-64 (1994).
Miller Targeted vectors for gene therapy. The FASEB Journal 9:190-9 (1995).
Orkin et al., Report and Recommendations of the Panel to Assess the NIH Investment in Research on Gene Therapy. www.nih.gov Dec. 1995.
Verma et al., Gene therapy—promises, problems and prospects. Nature 389:239-242 (1997).
Chang, Zongli et al: "A replication-competent feline leukemia virus, subgroup a (FeLV-A), tagged with green fluorescent protein reporter exhibits in vitro biological properties similar to those of the parental FeLV-A." Journal of Virology, vol. 75, No. 18, Sep. 2001, pp. 8837-8841.
Chang, Lung-Ji et al: "Human immunodeficiency viruses containing heterologous enhancer/promoters are replication competent and exhibit different lymphocyte tropisms." Journal of Virology, vol. 67, No. 3, Feb. 1993, pp. 743-752.
Fassati, et al: "Insertion of two independent enhancers in the long terminal repeat of a self-inactivating vector results in high-titer retroviral vectors with tissue-specific expression." Human Gene Therapy vol. 9, 1998, pp. 2459-2468.
Logg, Christopher R et al: "A uniquely stable replication-competent retrovirus vector achieves efficient gene delivery in vitro and in solid tumors" Human Gene Therapy, vol. 12, No. 8, May 20, 2001, pp. 921-932.
Logg, Christopher R et al: "Tissue-specific transcriptional targeting of a replication-competent retroviral vector." Journal of Virology, vol. 76, No. 24, Dec. 2002, pp. 12783-12791.
Tai, Chien-Kou et al: "Single-shot, multicycle suicide gene therapy by replication-competent retrovirus vectors achieves long-term survival benefit in experimental glioma." Molecular Therapy, vol. 12, No. 5, Nov. 2005, pp. 842-851.
Xie et al., "Enhanced Retinal Ganglion Cell Differentiation by ath5 and NSCL1 Coexpression," IOVS 45(9):2922-2928 (2004).
Yamashita et al., "The cell cycle independence of HIV infections is not determined by known karyophilic viral elements," PLoS Pathog. 1:e18 (2005).
Yap et al., "Trim5alpha protein restricts both HIV-1 and murine leukemia virus," Proc. Natl. Acad. Sci. USA 101:10786-10791 (2004).
Yi, et al., "Retroviral gene therapy: safety issues and possible solutions," Curr. Gene Ther. 5:25-35 (2005).
Young et al., "Chimeric Retroviral Helper Virus and Picornavirus IRES Sequence to Eliminate DNA Methylation for Improved Retroviral Packaging Cells," J. Virol. 74(11):5242-5249 (2000).
Young, Lee W. International Search Report and Written Opinion. International Application No. PCT/US2009/049322. Date of mailing: Sep. 2, 2009.
Zhang, J., et al., A Novel Oncolytic Adenovirus Expressing Escherichia coli Cytosine Deaminase Exhibits Potent Antitumor Effect on Human Solid Tumors; Cancer Biotherapy and Radiopharmaceuticals; vol. 25, No. 4, 2010; pp. 487-495; Mary Ann Liebert, Inc.
Bushman et al., "Sequence Requirements for Integration of Moloney Murine Leukemia Virus DNA In Vitro", J Virol, 1990, 64: 5645-5648.

(56) References Cited

OTHER PUBLICATIONS

Cepko et al., "Transduction of Genes Using Retrovirus Vectors", Current Protocols in Molecular Biology, 1996, Chapter 9: Unit 9.9; 9.91-9.916.

Nishiyama, T. et al., Antineoplastic Effects in Rats of 5-Fluorocytosine in Combination with Cytosine Deaminase Capsules; Cancer Res 1985;45:1753-1761; American Association for Cancer Research.

Nogues et al., "Transcriptional activators differ in their abilities to control alternative splicing," J. Biol. Chem. 277:43110-43114 (2002).

Nyati, M. et al., High and Selective Expression of Yeast Cytosine Deaminase under a Carcinoembryonic Antigen Promoter-Enhancer; Cancer Res 2002;62:2337-2342; American Association for Cancer Research.

Fogar, P. et al., "Suicide Gene Therapy With the Yeast Fusion Gene Cytosine Deaminase/Uracil Phosphoribosyltransferase Is Not Enough for Pancreatic Cancer", Pancreas, vol. 35, No. 3, Oct. 2007; 224-231; Lippincott Williams & Wilkins.

O'Reilly et al., "Second-site changes affect viability of amphotropic/ecotropic chimeric enveloped murine leukemia viruses," J. Virol. 74:899-913 (2000).

Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).

Owens et al., "Human and simian immunodeficiency virus capsid proteins are major viral determinants of early, postentry replication blocks in simian cells," J. Virol. 77:726-731 (2003).

Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).

Paar et al., "Influence of vector design and host cell on the mechanism of recombination and emergence of mutant subpopulations of replicating retroviral vectors," BMC Molecular Biology 10(8) (2009).

Pao et al., "Use of avian retroviral vectors to introduce transcriptional regulators into mammalian cells for analyses of tumor maintenance," PNAS 100(15):8764-8769.

Poltoratsky, V., Recombinogenic Phenotype of Human Activation-Induced Cytosine Deaminas; J Immunol 2004; 172:4308-4313; http://www.jimmunol.org/content/172/7/4308; The American Association of Immunologists, Inc.

Poon et al. "Nucleocapsid and matrix protein contributions to selective human immunodeficiency virus type 1 genomic RNA packaging," J. Virol. 72:1983-1993 (1998).

Qiao et al. "VSV-G pseudotyped, MuLV-based, semi-replication-competent retrovirus for cancer treatment. Gene Ther," 13:1457-1470 (2006).

Rainov et al., "Clinical trials with retrovirus mediated gene therapy—what have we learned?," J. Neurooncol. 65:227-236 (2003).

Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).

Robson et al., "Selection of optimal polypurine tract region sequences during Moloney murine leukemia virus replication," J. Virol. 74:10293-10303 (2000).

Roscigno et al., "A mutational analysis of the polypyrimidine tract of introns. Effects of sequence differences in pyrimidine tracts on splicing," J. Biol. Chem. 268:11222-11229 (1993).

Saavedra et al., "The simian retrovirus-1 constitutive transport element, unlike the HIV-1 RRE, uses factors required for cellular mRNA export," Curr. Biol. 7:619-628 (1997).

Sanders, D. A. "No false start for novel pseudotyped vectors," Curr. Opin. Biotechnol. 13, 437-442 (2002).

Segall et al., "Characterization and Detection of Artificial Replication-Competent *Lentivirus* of Altered Host Range," Molecular Therapy 8:118-129 (2003).

Shen, H. et al., Targeting of the Activation-Induced Cytosine Deaminase Is Strongly Influenced by the Sequence and Structure of the Targeted DNA; Molecular and Cellular Biology, Dec. 2005, p. 10815-10821 vol. 25, No. 24; doi:10.1128/MCB.25.24.10815-10821.2005; American Society for Microbiology.

Shikova-Lekova et al. "Replication-competent hybrids between murine leukemia virus and foamy virus," J. Virol. 77, 7677-7681 (2003).

Shin et al., "Replication of lengthened Moloney murine leukemia virus genomes is impaired at multiple stages," J. Virol. 74:2694-2702 (2000).

Short et al., "Correlation of leukemogenic potential of murine retroviruses with transcriptional tissue preference of the viral long terminal repeats," J. Virol. 61:1067-1072 (1987).

Sliva et al., "Stable integration of a functional shRNA expression cassette into the murine leukemia virus genome," Virology 351(1):218-225 (2006).

Sodroski et al., "Repetitive structure in the long-terminal-repeat element of a type II human T-cell leukemia virus," Proc. Natl. Acad. Sci. USA 81:4617-4621. 1984.

Soifer et al., "A Novel, Helper-Dependent, Adenovirus-Retrovirus Hybrid Vector: Stable Transduction by a Two-Stage Mechanism," Molecular Therapy 5(5):599-608 (2002).

Solly et al., "Replicative retroviral vectors for cancer gene therapy," Cancer Gene Ther. 10:30-39 (2003).

Sotos, G. et al., Preclinical and clinical aspects of biomodulation of 5-fluorouracil; Cancer Treatment Reviews (1994) 20, 11-49; W. B. Saunders.

Staffa et al., Identification of positive and negative splicing regulatory elements within the terminal tat-rev exon of human immunodeficiency virus type 1. Mol. Cell Biol. 15:4597-4605 (1995).

Stolworthy, T., et al., Yeast Cytosine Deaminase Mutants with Increased Thermostability Impart Sensitivity to 5-Fluorocytosine; J Mol Biol. Mar. 28, 2008; 377(3): 854-869; National Institutes of Health.

Subramanian et al., "Temperature-sensitive replication-competent adenovirus shRNA vectors to study cellular genes in virus-induced apoptosis," Methods in Molecular Medicine 130:125-134 (2007).

Sun et al., "Chronic gene delivery of interferon-inducible protein 10 through replication competent retrovirus vectors suppresses tumor growth," Cancer Gene Ther. 12:900-912 (2005).

Svarovskaia et al., Retroviral mutation rates and reverse transcriptase fidelity, Front. Biosci. 8:d117-d134 (2003).

Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.

Tai et al., "Antibody-Mediated Targeting of Replication-Competent Retroviral Vectors," Human Gene Therapy 14:789-802 (2003).

Tai et al., "Replication-competent retrovirus vectors for cancer gene therapy," Frontiers in Bioscience 13:3083-95 (2008).

Takeuchi et al., "Type C retrovirus inactivation by human complement is determined by both the viral genome and the producer cell," J. Virol. 68: 8001-8007 (1994).

Trubetskoy et al., "R region sequences in the long terminal repeat of a murine retrovirus specifically increase expression of unspliced RNAs," J. Virol. 73:3477-3483 (1999).

Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).

Van Santen et al., "mRNA precursor splicing in vivo: sequence requirements determined by deletion analysis of an intervening sequence," Proc. Natl Acad. Sci. USA 82:2885-2889 (1985).

Wallace, P. et al., Intratumoral Generation of 5-Fluorouracil Mediated by an Antibody-Cytosine Deaminase Conjugate in Combination with 5-Fluorocytosine; Cancer Res 1994;54:2719-2723; American Association for Cancer Research.

Wang et al., "Highly Efficient and Tumor-Restricted Gene Transfer to Malignant Gliomas by Replication-Competent Retroviral Vectors," Human Gene Therapy 14:117-127 (2003).

(56) References Cited

OTHER PUBLICATIONS

Wang, W. et al., Use of replication-competent retroviral vectors in an immunocompetent intracranial glioma model; Neurosurg. Focus; vol. 20; Apr. 2006; pp. 1-9.
Wang et al., "A murine leukemia virus with Cre-LoxP excisible coding sequences allowing superinfection, transgene delivery, and generation of host genomic deletions," Retrovirology 1(5) (2004).
Warmann et al., "Adenovirus-mediated cytosine deaminase/5-fluorocytosine suicide gene therapy of human hepatoblastoma in vitro," Pediatric Blood & Cancer, 53: 145-151 (2009).
Xie et al., "Adenovirus-mediated tissue-targeted expression of a caspase-9-based artificial death switch for the treatment of prostate cancer," Cancer Res. 61:6795-6804 (2001).
Aagaard et al., "Fv1-like restriction of N-tropic replication-competent murine leukaemia viruses in mCAT-1-expressing human cells," Journal of General Virology 83:439-442 (2002).
Addison et al., "Comparison of the human versus murine cytomegalovirus immediate early gene promoters for transgene expression by adenoviral vectors," J. Gen. Virol. 78:1653-1661 (1997).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Akimoto, M. et al., A new delivery system for 5-fluorouracil using prodrug and converting enzyme; Laboratory Science; Br J Ophthalmol 2002;86:581-586; www.bjophthalmol.com.
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick et al., "Splicing mediates the activity of four putative cellular internal ribosome entry sites," PNAS 105(12):4733-4738 (2008).
Barsov et al., "Adaptation of chimeric retroviruses in vitro and in vivo: isolation of avian retroviral vectors with extended host range," J. Virol. 75:4973-4983 (2001).
Beijer, Gijsbertus. International Preliminary Report on Patentability. International Application No. PCT/US2009/058510. Date of mailing: Apr. 7, 2011.
Beijer, Gijsbertus. International Preliminary Report on Patentability. International Application No. PCT/US2009/058512. Date of Mailing: Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56 (1999).
Cherry et al., "Retroviral Expression in Embryonic Stem Cells and Hematopoietic Stem Cells," Molecular and Cellular Biology 20(20):7419-7426 (2000).
Chio, Jun Ho. International Search Report and Written Opinion. International Application No. PCT/US2009/058510. Date of mailing of the International Search Report Jul. 6, 2010.
Cho, Jeong Han. International Search Report and Written Opinion. International Application No. PCT/US2009/058512. Date of mailing of the Report: May 11, 2011.
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-region sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.
Erbs, P., et al., Characterization of the *Saccharomyces cerevisiae* FCY1 gene encoding cytosine deaminase and its homologue FCA1 of *Candida albicans*; Curr Genet 31: 1-6; Springer-Verlag 1997.
Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, xenotropic, and amphotropic murine leukemia viruses," J. Virol. 64: 6176-6183 (1990).
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.

(56) References Cited

OTHER PUBLICATIONS

Freytag et al., "Phase I Study of Replication-competent Adenovirus-mediated Double Suicide Gene Therapy for the Treatment of Locally Recurrent Prostate Cancer," Cancer Res. 62:4968 (2002).
Garton et al., "Efficient Expression of Exogenous Genes in Primary Vascular Cells Using IRES-Based Retroviral Vectors," Biotechniques 32:830-843 (2002).
Gene-Bank-AAG33626; cytosine deaminase-uracil phosphoribosylransferase fusion protein [synthetic contruct]; Gene-Bank-AAG33626; pp. 1-2; http://www.ncbi.nlm.nih.gov/protein/AAg33626.
Gene-Bank-Y1SB__A; Chain A, Yeast Cytosine Deaminase Triple Mutant; pp. 1-2; http://www.ncbi.nlm.nih.gov/protein/1ySB__A.
Giffo-Schmitt, Beate. International Preliminary Report on Patentability. International Application No. PCT/US2009/049322. Date of Issuance of Report: Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Horn et al., "Highly efficient gene transfer into baboon marrow repopulating cells using GALV-pseudotype oncoretroviral vectors produced by human packaging cells," Blood 100:3960-3967 (2002).
Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).
Hughes, Stephen H., "The RCAS Vector System," Folia Biologica (Praha) 50(3-4):107019 (2004).
Ireton, G. et al., The Structure of *Escherichia coli* Cytosine Deaminase; J. Mol. Biol. (2002) 315, Academic Press; 687-697.
Ireton, G. et al., The 1.14A° Crystal Structure of Yeast Cytosine Deaminase: Evolution of Nucleotide Salvage Enzymes and Implications for Genetic Chemotherapy; Structure, vol. 11, 961-972, Aug. 2003, Elsevier Science Ltd.
Johann et al., "Definition of a domain of GLVR1 which is necessary for infection by gibbon ape leukemia virus and which is highly polymorphic between species," J. Virol. 67:6733-6736 (1993).
Kaliberov et al., "Mutation of *Escherichia coli* cytosine deaminase significantly enhances molecular chemotherapy of human glioma," Gene Ther. 14(14):1111-9; Epub May 10, 2007.
Kaliberova et al., "Molecular chemotherapy of pancreatic cancer using novel mutant bacterial cytosine deaminase gene," 7(9):2845-54 (2008).
Kawasaki et al., "Replication-competent retrovirus vector-mediated prodrug activator gene therapy in experimental models of human malignant mesothelioma," Cancer Gene Therapy 18:571-578 (2011).
Kern, L et al., The FUR1 gene of Sacckaromyces ceret, isiae: cloning, structure and expression of wild-type and mutant alleles; Gene, 88 (1990) 149-157; 1990 Elsevier Science Publishers B.V. (Biomedical Division).

Kikuchi et al., "Highly Efficient Gene Delivery for Bladder Cancers by Intravesically Administered Replication-Competent Retroviral Vectors," Clin. Cancer Res. 13:4511-4518 (2007).
Klein et al., "Rapid identification of viable retrovirus-transduced cells using the green fluorescent protein as a marker," Gene Ther. 4:1256-1260 (1997).
Korkegian, A. et al., Computational Thermostabilization of an Enzyme; Science vol. 308; May 6, 2005; 857-860; www.sciencemag.org.
Kornblihtt et al., "Multiple links between transcription and splicing," RNA 10:1489-1498 (2004).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lazo et al., "Splice acceptor site for the env message of Moloney murine leukemia virus," J. Virol. 61:2038-2041 (1987).
Lipinski et al., "Optimization of a synthetic beta-catenin-dependent promoter for tumor-specific cancer gene therapy," Mol. Ther. 10:150-161 (2004).
Liu et al., "Tumor-specific therapeutic effect induced by an oncolytic adenoviral vector containing heat shock protein 70 and prodrug activation genes," 13(16):1235-43; Epub Apr. 13, 2006.
Liu et al. "Engineering conditionally replication-competent adenoviral vectors carrying the cytosine deaminase gene increase the infectivity and therapeutic effect for breast cancer gene therapy," 13(4):346-56 (2006).
Liu et al., "The receptors for gibbon ape leukemia virus and amphotropic murine leukemia virus are not downregulated in productively infected cells," Retrovirology 8:53 (2011).
Logg et al., "Genomic Stability of Murine Leukemia Viruses Containing Insertions at the Env-3' Untranslated Region Boundary," Journal of Virology 75(15):6989-6998 (2001).
Logg et al., "Retrovirus-Mediated Gene Transfer to Tumors," Methods in Molecular Biology 246:499-525 (2004).
Lu et al., "Highly efficient gene transfer to solid tumors in vivo by tumor-selective replicating retrovirus vectors," Int. J. Mol. Med. 25(5):769-75 (2010).
Maguire, Simon. Examination Report. New Zealand Application No. 592070. Date of Report: May 24, 2011.
Yin, "Insertion of sequences into the 3' untranslated region of a replication-competent spleen necrosis virus vector disrupts env gene expression," Arch Viol. (1999) 14:73-87.
Mahan, S. et al., Random mutagenesis and selection of *Escherichia coli* cytosine deaminase for cancer gene therapy; Protein Engineering, Design & Selection vol. 17 No. 8 pp. 625-633, 2004;Published online Sep. 20, 2004.
Mahan, S. et al., Alanine-Scanning Mutagenesis Reveals a Cytosine Deaminase Mutant with Altered Substrate Preference; Biochemistry 2004, 43, 8957-8964; American Chemical Society.
Malim et al., "The HIV-1 rev trans-activator acts through a structured target sequence to activate nuclear export of unspliced viral mRNA," Nature 338:254-257 (1989).
Marzio et al., "In vitro evolution of a highly replicating, doxycycline-dependent HIV for applications in vaccine studies," Proc. Natl Acad. Sci. USA 98:6342-6347 (2001).
Metzl et al., "Tissue- and Tumor-Specific Targeting of Murine Leukemia Virus-Based Replication-Competent Retroviral Vectors," Journal of Virology 80(14):7070-7078 (2006).
Mild et al., "Frequent intrapatient recombination between human immunodeficiency virus type 1 R5 and X4 envelopes: implications for coreceptor switch," J. Virol. 81:3369-3376 (2007).
Miller et al., "Gene transfer by retrovirus vectors occurs only in cells that are actively replicating at the time of infection," Mol. Cell. Biol. 10:4239-4242 (1990).
Miller et al., "Construction and properties of retrovirus packaging cells based on gibbon ape leukemia virus," J. Virol. 65:2220-2224 (1991).
Miller et al., "Intratumurol 5-Fluorouracil Produced by Cytosine Deaminase/5-Fluorocytosine Gene Therapy Is Effective for Experimental Human Glioblastomas," Cancer Res. 62:773 (2002).

(56) References Cited

OTHER PUBLICATIONS

Mullen et al., "Transfer of the bacterial gene for cytosine deaminase to mammalian cells confers lethal sensitivity to 5-fluorocytosine: a negative selection system," PNAS 89(1):33-37 (1992).

Mukesh et al., "High and Selective Expression of Yeast Cytosine Deaminase Under a Carcinoembryonic Antigen Promoter-Enhancer," Cancer Res. 62:2337-2342 (2002).

Nack et al., "Replacement of the murine leukemia virus (MLV) envelope gene with a truncated HIV envelope gene in MLV generates a virus with impaired replication capacity," Virology 315:209-216 (2003).

Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.

Naldini et al., "Efficient transfer, integration, and sustained long-term expression of the transgene in adult rat brains injected with a lentiviral vector," Proc. Natl. Acad. Sci. USA 93:11382-11388 (1996).

Negroni et al., "Treatment of colon cancer cells using the cytosine deaminase/5-fluorocytosine suicide system induces apotosis, modulation of the proteome, and Hsp90B phsopholylation," Molecular Cancer Therapeutics 6:2747-2756 (2007).

\* cited by examiner g1ZD-GFP

| env | | IRES |
...AGAGTACGAGCCATAGATAACGTTACTGGCC...
| IRES | | GFP |
...CACGATAATACCATGGCCATTCGAACAAAGG...
| GFP | | MLV NONCODING |
...CTGTACAAGTAGCGGCCGCGCCATAGATAAA...

g1ZD-hygro

| env | | IRES |
...AGAGTACGAGCCATAGATAACGTTACTGGCC...
| IRES | | hygromycin R |
...CACGATAATACCATGGCCATTCGAACCGCGA...
| hygromycin R | | MLV NONCODING |
...TGGGGGCCGCGCCATAGATAAAATAAAGAT...

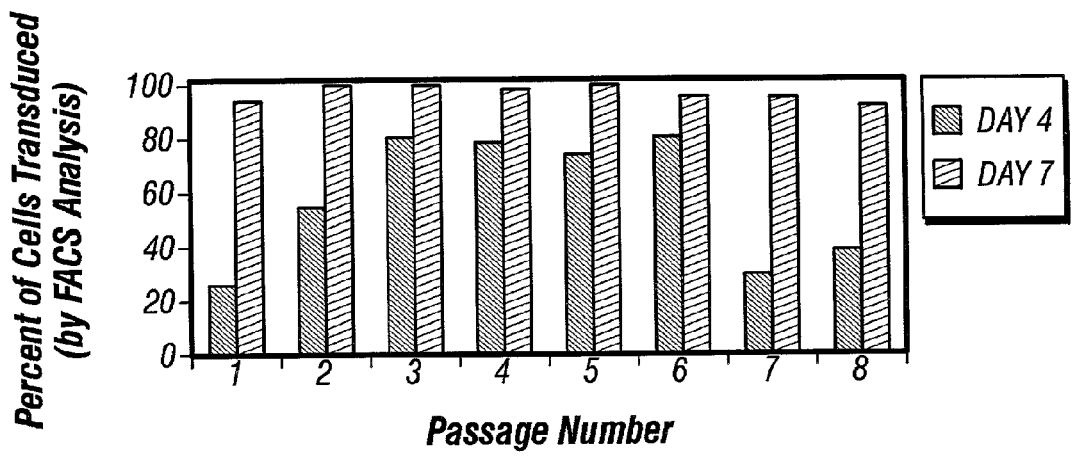
FIG. 5
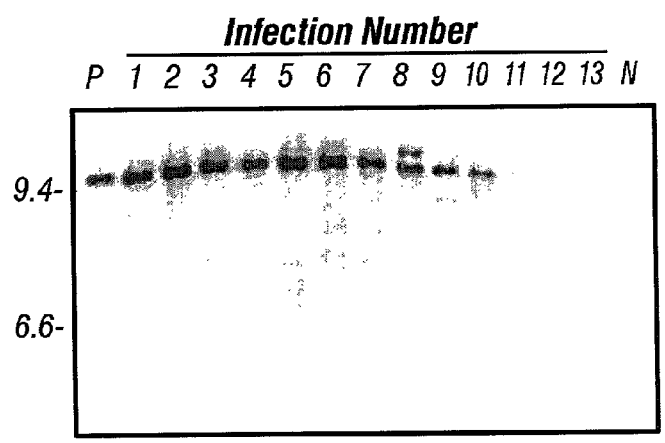
FIG. 6A
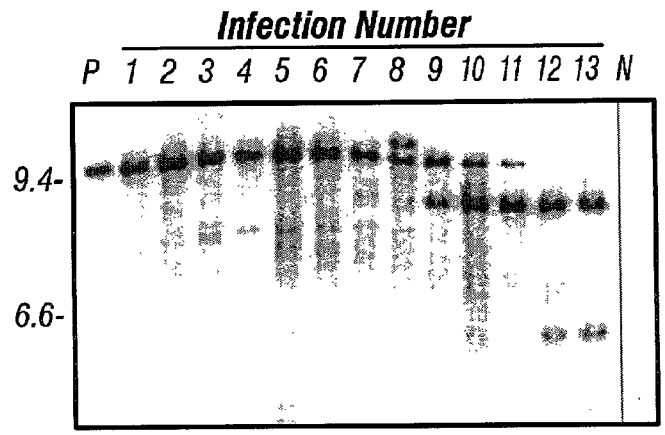

ZE-GFP

ZV-A-GFP

WILD TYPE MLV ENVELOPE

ZDAH-emd

ZBAH-emd

SEQUENCE LISTING

<160> NUMBER OF SEQ ID NOS: 8

<210> SEQ ID NO 1
<211> LENGTH: 24
<212> TYPE: DNA
<213> ORGANISM: Mouse

<400> SEQUENCE: 1
atccacagtt caggttcaat ggcg					24

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
ctgctacctt ctttttga					18

<210> SEQ ID NO 3
<211> LENGTH: 24
<212> TYPE: DNA
<213> ORGANISM: Mouse

<400> SEQUENCE: 3
gattcttgtc tgtcatcata ctgg					24

```
<210> SEQ ID NO 4
<211> LENGTH: 31
<212> TYPE: DNA
<213> ORGANISM: homo sapien

<400> SEQUENCE: 4
agagtacgag ccatagataa cgttactggc c                               31

<210> SEQ ID NO 5
<211> LENGTH: 31
<212> TYPE: DNA
<213> ORGANISM: homo sapien

<400> SEQUENCE: 5
cacgataata ccatggccat tcgaacaaag g                               31

<210> SEQ ID NO 6
<211> LENGTH: 31
<212> TYPE: DNA
<213> ORGANISM: Homo sapien

<400> SEQUENCE: 6
ctgtacaagt agcggccgcg ccatagataa a                               31

<210> SEQ ID NO 7
<211> LENGTH: 31
<212> TYPE: DNA
<213> ORGANISM: Homo sapien

<400> SEQUENCE: 7
cacgataata ccatggccat tcgaaccgcg a                               31

<210> SEQ ID NO 8
<211> LENGTH: 31
<212> TYPE: DNA
<213> ORGANISM: Homo sapien

<400> SEQUENCE: 8
tgggggccgc gccatagata aaataaaaga t                               31
```

GENE DELIVERY SYSTEM AND METHODS OF USE

CROSS REFERENCE TO RELATED APPLICATIONS

This application is a Continuing Application of Ser. No. 09/409,650, filed Oct. 1, 1999 (now issued as U.S. Pat. No. 6,410,313 on Jun. 25, 2002), which claims priority from Provisional Application Ser. No. 60/102,933, filed Oct. 1, 1998, to which application a priority claim is made under 35 U.S.C. §119(e). The related applications are incorporated by reference herein in their entirety.

FIELD OF THE INVENTION

The present invention relates generally to the field of viral vectors and specifically to a novel recombinant replication competent retrovirus useful for the transfer and expression of nucleic acid sequences in a targeted cell.

BACKGROUND OF THE INVENTION

The development of genetic vectors has heralded the fast-growing field of somatic gene transfer. (Anderson, W. F., *Science*, 1984, 226:401-409). Vectors based on simple retroviruses, such as the Moloney Leukemia Virus (MoMLV), are often selected because they efficiently integrate into the genome of the target cell. Integration is thought to be a prerequisite for long-term expression of the transduced gene. However, efficient gene transfer to tumor tissue has been a major impediment to treatment of cell proliferative disorders despite the use of viral vectors such as retroviruses.

In the early steps of infection, retroviruses deliver their nucleoprotein core into the cytoplasm of the target cell. Here, reverse transcription of the viral genome takes place while the core matures into a preintegration complex. The complex must reach the nucleus to achieve integration of the viral DNA into the host cell chromosomes. For simple retroviruses (oncoretroviruses), this step requires the dissolution of the nuclear membrane at mitotic prophase, most likely because the bulky size of the preintegration complex prevents its passive diffusion through the nuclear pores because there are no nuclear localization signals to facilitate active transport into the nucleus.

Currently retroviral vectors used for human gene therapy are replication-defective and must be produced in packaging cells, which contain integrated wild type virus genome sequences and thus provide all of the structural elements necessary to assemble viruses (i.e., the gag, pol, and env gene products), but cannot encapsidate their own wild type virus genomes due to a deletion of the packaging signal sequence (psi). Replication-defective virus vectors created by removal of the viral structural genes and replacement with therapeutic genes are introduced into the packaging cells; so long as these vectors contain the psi signal, they can take advantage of the structural proteins provided by the cells and be encapsidated into virion. However, after infection of a target cell, the vectors are incapable of secondary horizontal infections of adjacent cells due to the deletion of the essential viral genes.

The use of replication-defective vectors has been an important safeguard against the uncontrolled spread of virus, as replication-competent retroviruses have been shown to cause malignancies in primates (Donahue et al., *J. Exp. Med.*, 1992, 176:1124-1135). However, replication-defective retroviral vectors are produced from the packaging cells at titers on the order of only $10^{6-7}$ colony-forming units (cfu) per ml, which is barely adequate for transduction in vivo. In fact, clinical trials for gene therapy of glioblastoma multiforme, a highly malignant brain tumor, have encountered major problems in achieving adequate levels of tumor cell transduction, and despite promising initial results in animal studies (Culver et al., *Science*, 1992, 256:1550-1552). In order to increase transduction levels as much as possible, instead of using a single shot of virus-containing supernatant, the virus packaging cell line PA317 itself was injected into the brain tumors to constitutively produce retrovirus vectors carrying the HSV-tk gene (Oldfield et al., *Human Gene Therapy*, 1993, 4:39-69). Subsequently, the protocol was further modified to include a debulking procedure followed by multiple injection sites, as it was found that the virus vectors did not diffuse far enough from the site of initial injection. Despite these modifications, the transduction efficiency has been estimated to less than 1% of the tumor cell mass and any significant tumor destruction is presumed to be due to the potent bystander effect of the HSV-tk/ganciclovir treatment. Thus efficient transduction of cancer cells in a solid tumor mass represents a major problem for cancer gene therapy.

Accordingly, there is a need for a gene transfer vector capable of high-level transduction in vivo, while limiting uncontrolled spread of replication-competent virus which could result in insertional mutagenesis and carcinogenesis.

SUMMARY OF THE INVENTION

The present invention provides recombinant replication competent retroviral vectors for gene delivery. The vectors provide a high-level of transduction in vivo. The use of replication-competent vectors of the invention allow efficient in vivo transduction. The incorporation of cell-type targeting polynucleotide sequences into such vectors reduce or eliminate the native pathogenic potential of replication-competent retroviruses while improving their target cell specificity.

In one embodiment, the present invention provides a recombinant replication competent retrovirus having a retroviral GAG protein; a retroviral POL protein; a retroviral ENV protein; a retroviral genome comprising Long-Terminal Repeat (LTR) sequences at the 5' and 3' ends of the retroviral genome, wherein a target specific polynucleotide sequence is contained within the LTR sequences at the 5' and/or 3' end of the retroviral genome, a heterologous nucleic acid sequence operably linked to a regulatory nucleic acid sequence; and cis-acting nucleic acid sequences, and sequences encoding proteins, necessary for reverse transcription, packaging and integration in a target cell. The target specific polynucleotide sequence of the retroviral vector can be a tissue-specific promoter sequence, for example a sequence associated with a growth regulatory gene, such as, for example, probasin. To target the retrovirus to a specific cell or tissue the retrovirus ENV protein can further comprise a target-specific ligand sequence, which encodes, for example, an antibody, receptor, or ligand, such as, heregulin.

In another embodiment, the present invention provides a recombinant retroviral polynucleotide sequence, having a polynucleotide sequence encoding a GAG protein; a polynucleotide sequence encoding a POL protein; a polynucleotide sequence encoding an ENV protein; a polynucleotide sequence comprising a Long Terminal Repeat (LTR) at the 5' and 3' end of the retroviral polynucleotide sequence containing a target specific polynucleotide sequence at the 5' and or 3' end; a heterologous polynucleotides sequence operably linked to a regulatory nucleic acid sequence; and cis acting polynucleotide sequence, as well as sequences encoding proteins, necessary for reverse transcription, packaging and integration in a target cell. The target specific polynucleotide sequence is a cell- or tissue-specific promoter sequence such as, for example, one associated with a growth regulatory gene or one associated with a cancer marker (e.g., probasin). The ENV sequence may be further associated with a target-specific ligand polynucleotide sequence, for example a sequence encoding an antibody, a receptor (e.g., a hormone receptor), or a ligand, such as, for example, heregulin.

In yet another embodiment, the present invention provides, a method of treating a subject having a cell proliferative disorder, by contacting the subject with a retrovirus, having a retroviral GAG protein; a retroviral POL protein; a retroviral ENV protein; a retroviral genome comprising Long-Terminal Repeat (LTR) sequences at the 5' and 3' end of the retroviral genome, wherein a target specific polynucleotide sequence is contained within the LTR sequences at the 5' and/or 3' end of the retroviral genome, a heterologous nucleic acid sequence operably linked to a regulatory nucleic acid sequence; and cis-acting nucleic acid sequences, as well as sequence encoding proteins, necessary for reverse transcription, packaging and integration in a target cell. The target cell is preferably a cell having a cell proliferative disorder, such as a neoplastic cell.

These and other aspects of the present invention will be apparent to those of skill in the art from the teachings herein.

BRIEF DESCRIPTION OF THE FIGURES

FIG. 3B shows a comparison of Replication Kinetcs of Replication-competent Vectors and Wild Type Mo-MLV in Cultured Cells.

FIG. 5 is a graph depicting the stability of GFP transgene expression from the replication-competent gIZD-GFP vector over multiple serial passages.

DETAILED DESCRIPTION OF THE INVENTION

Figure 1A:
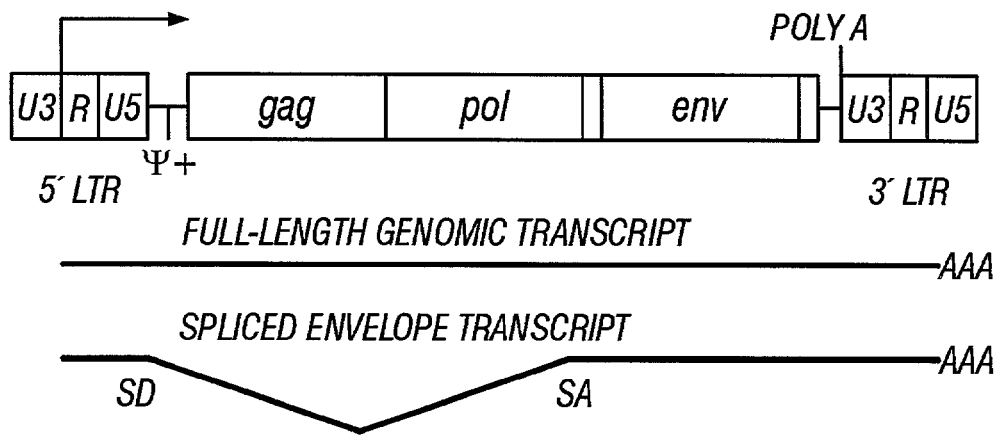
FIG. 1 (A) is a schematic illustration of the structure of wild type (replication-competent) MoMLV retrovirus; LTR=long terminal repeat. (B) is a schematic representation of g1ZD-GFP and g1ZD-hygro, showing the sizes of the IRES-transgene cassettes and the site of their insertion into the wild-type MLV genome. Arrows indicate location of NheI sites used to digest DNA for Southern hybridization analysis, and wavy lines indicate regions of the vectors probed in hybridization analysis. Also shown is the sequences of g1ZD-GFP and g1ZD-hygro at locations between env gene and IRES, IRES and GFP, and GFP and 3' LTR. Bold letters indicate start or stop codons present within the junctions.

To facilitate understanding of the invention, a number of terms are defined below.

"Polynucleotide" or "nucleic acid sequence" refers to a polymeric form of nucleotides at least 9 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA or RNA which is incorporated into a viral vector. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein can also refer to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

The present invention provides a recombinant replication-competent retrovirus capable of infecting targeted cells. The virus is useful for the in vivo and ex vivo transfer and expression of genes and nucleic acid sequences (e.g., in dividing and non-dividing cells). In particular, the present retroviral vectors are useful in targeting specific cell types including, but not limited to, neoplastic cells or cells having cell-proliferative disorders.

The present invention has many utilities. For example, the retrovirus and methods of the present invention can be used to provide a therapeutic product to a subject, for providing gene delivery of a non-therapeutic protein or a therapeutic protein to a subject, as well as in in vitro studies to provide a cell with a gene for expression of a gene product. Such in vitro methods are useful, for example, in protein production and the study of regulation and interaction of cis-acting products, and polypeptides.

Retroviruses

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The family Retroviridae are enveloped single-stranded RNA viruses that typically infect mammals, such as, for example, bovines, monkeys, sheep, and humans, as well as avian species. Retroviruses are unique among RNA viruses in that their multiplication involves the synthesis of a DNA copy of the RNA which is then integrated into the genome of the infected cell.

The Retroviridae family consists of three groups: the spumaviruses (or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses are further subdivided into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of ~75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRS. A duplication of cellular sequences is seen at the ends of both LTRs, reminiscent of the integration pattern of transposable genetic elements. Integration is thought to occur essentially at random within the target cell genome. However, by modifying the long-terminal repeats it is possible to control the integration of a retroviral genome.

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is important in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

Replication Competent Recombinant Retroviruses

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the present invention, since the sequences for encapsidation are provided in the genome thus providing a replication competent retroviral vector for gene delivery or therapy.

The retroviral genome and the proviral DNA of the present invention have at least three genes: the gag, the pol, and the env, which are flanked by two long terminal repeat (LTR) sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

In a first embodiment, the invention provides a recombinant retrovirus capable of infecting a non-dividing cell, a dividing cell, or a cell having a cell proliferative disorder. The recombinant replication competent retrovirus of the present invention comprises a polynucleotide sequence having a viral GAG, a viral POL, a viral ENV, a heterologous polynucleotide and one or more targeting polynucleotide sequence for cell- or tissue-specific targeting of the retrovirus to a particular tissue, cell or cell type, as described herein.

The heterologous nucleic acid sequence is operably linked to a regulatory nucleic acid sequence. As used herein, the term "heterologous" nucleic acid sequence or transgene refers to a sequence that does not normally exist in the wild (e.g., in the wild-type retrovirus) or a sequence that originates from a foreign species, or, if from the same species, it may be substantially modified from its original form. Alternatively, an unchanged nucleic acid sequence that is not normally expressed in a cell is a heterologous nucleic acid sequence.

Depending upon the intended use of the retroviral vector of the present invention any number of heterologous polynucleotide or nucleic acid sequences may be inserted into the retroviral vector. For example, for in vitro studies commonly used marker genes or reporter genes may be used, including, antibiotic resistance and fluorescent molecules (e.g., GFP). Additional polynucleotide sequences encoding any desired polypeptide sequence may also be inserted into the vector of the present invention. Where in vivo delivery of a heterologous nucleic acid sequence is sought both therapeutic and non-therapeutic sequences may be used. For example, the heterologous sequence can encode a therapeutic molecule including antisense molecules or ribozymes directed to a particular gene associated with a cell proliferative disorder, the heterologous sequence can be a suicide gene (e.g., HSV-tk or PNP), or a therapeutic protein (e.g., Factor IX). Other therapeutic proteins applicable to the present invention are easily identified in the art (see for example, R. Crystal, *Science* 270:404-410 (1995)).

Thus, the recombinant virus of the invention is capable of transferring a nucleic acid sequence into a target cell. The term nucleic acid sequence refers to any nucleic acid molecule, including DNA, RNA or modified nucleic acid sequences. The nucleic acid molecule may be derived from a variety of sources, including DNA, cDNA, synthetic DNA, RNA, or combinations thereof. Such nucleic acid sequences may comprise genomic DNA which may or may not include naturally occurring introns. Moreover, such genomic DNA may be obtained in association with promoter regions, introns, or poly A sequences. Genomic DNA may be extracted and purified from suitable cells by means well known in the art. Alternatively, messenger RNA (mRNA) can be isolated from cells and used to produce cDNA by reverse transcription or other means.

The term "regulatory nucleic acid sequence" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter. Preferably the regulatory sequences is an IRES sequence.

The term "operably linked" refers to functional linkage between the regulatory sequence and the heterologous nucleic acid sequence. The heterologous sequence can be linked to a promoter, resulting in a chimeric gene. The heterologous nucleic acid sequence is preferably under control of either the viral LTR promoter-enhancer signals or of an internal promoter, and retained signals within the retroviral LTR can still bring about efficient integration of the vector into the host cell genome. Accordingly, the recombinant retroviral vectors of the invention, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a regulatory sequence distal site (e.g., the IRES sequence 3' to the env gene). Other distal sites include viral promoter sequences, where the expression of the desired sequence or sequences is through splicing of the promoter proximal cistron, an internal heterologous promoter as SV40 or CMV, or an internal ribosome entry site (IRES).

In one embodiment, the retroviral genome of the present invention contains an IRES comprising a cloning site for insertion of a desired polynucleotide sequence, preferably the IRES is 3' to the env gene in the retroviral vector. Accordingly, a heterologous polynucleotide sequence encoding a desired polypeptide may be operably linked to the IRES. An example of polynucleotide sequence which may be operably linked to the IRES include green fluorescent protein (GFP) or a selectable marker gene. Marker genes are utilized to assay for the presence of the vector, and thus, to confirm infection and integration. Typical selection genes encode proteins that confer resistance to antibiotics and other toxic substances, e.g., histidinol, puromycin, hygromycin, neomycin, methotrexate, and other reporter genes known in the art. Other polynucleotide sequence which may be linked to the IRES include, for example, suicide genes, such as PNP and HSV-thymidine kinase (FIG. 2), polynucleotide sequences that encode an antisense molecule, or polynucleotides sequences that encode a ribosome.

It can be advantageous to have at one's disposal more efficacious gene therapy vectors capable, in particular, of producing several proteins of interest efficiently. However, the presence of several promoters within the same vector very often manifests itself in a reduction or even a loss of expression over time. This is due to a well-known phenomenon of interference between promoter sequences. In this context, the publication of International Application WO93/03143 proposes a solution to this problem which consists in employing an IRES. It describes a dicistonic retroviral vector for the expression of two genes of interest placed under the control of the same promoter. For example, the presence of a picornavirus IRES site between these genes permits the production of the expression product originating from the second gene of interest by internal initiation of the translation of the dicistronic mRNA (see Morgan et al., *Nucleic Acids Research*, 20:(6) 1293-1299 (1992)).

Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, *Mol. Cell. Biol.*, 8, 1103-1112) and the EMCV virus (encephalo-myocarditis virus (Jang et al., *J. Virol.*, 1988, 62, 2636-2643). The present invention provides the use of an IRES in the context of a replication-competent retroviral vector.

In another embodiment a targeting polynucleotide sequence is included as part of the recombinant retroviral vector of the present invention. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g.,MLV or lentivirus-derived). In another embodiment, the viral ENV protein is non-retrovirus-derived (e.g., CMV or VSV).

The recombinant retrovirus of the invention is therefore genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, neoplastic cells and others known in the art) such that the nucleic acid genome is delivered to a target non-dividing, a target dividing cell, or a target cell having a cell proliferative disorder. Targeting can be achieved in two ways. The first way directs the retrovirus to a target cell by preferentially binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome. The second method for targeting uses cell- or tissue-specific regulatory elements to preferentially promote expression and transcription of the viral genome in a targeted cell which actively utilizes the regulatory elements, as described more fully below. The transferred retrovirus genetic material is then transcribed and translated into proteins within the host cell. The targeting regulatory element is preferably linked to the 5' and/or 3' LTR, creating a chimeric LTR.

By inserting a heterologous nucleic acid sequence of interest into the viral vector of the invention, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the present invention, includes in one embodiment, a chimeric env protein comprising a retroviral env protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., *J. Of General Virol.*, 73, 3251-3255 (1992); Roux et al., *Proc. Natl. Acad. Sci USA* 86, 9079-9083 (1989)), recombinant virus containing in its envelope a sequence encoding a single-chain antibody variable region against a hapten (Russell et al., *Nucleic Acids Research*, 21, 1081-1085 (1993)), cloning of peptide hormone ligands into the retrovirus envelope (Kasahara et al., *Science*, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., *Proc. Natl. Acad. Sci USA*, 92, 7570-7574 (1995)), similarly the host range of ALV can be altered by incorporation of an integrin ligand, enabling the virus to now cross species to specifically infect rat glioblastoma cells (Valsesia-Wittmann et al., *J. Virol.* 68, 4609-4619 (1994)), and Dornberg and co-workers (Chu and Dornburg, *J. Virol* 69, 2659-2663 (1995)) have reported tissue-specific targeting of spleen necrosis virus (SNV), an avian retrovirus, using envelopes containing single-chain antibodies directed against tumor markers.

Figure 1B:
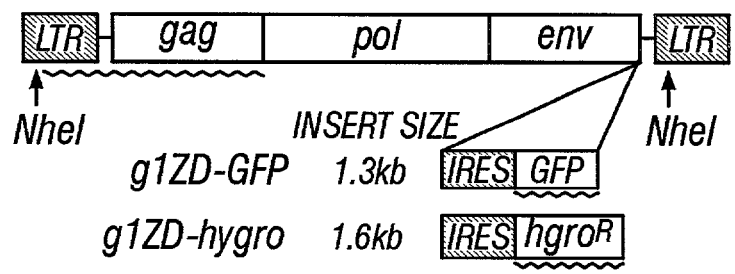
Figure 2A:
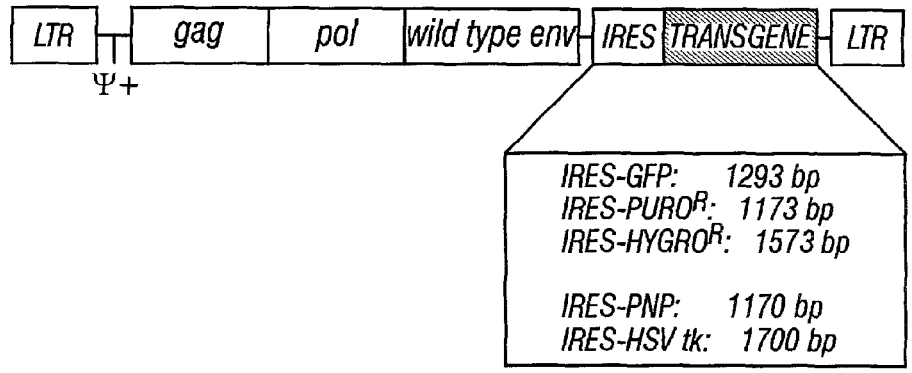
FIG. 2 is a schematic illustration of the structure of the modified MoMLV-based vectors of the present invention. A) A schematic diagram of the structure of MoMLV-based replication-competent retroviral (RCR) vectors containing an internal ribosome entry site (IRES). B) A schematic diagram of a targeted replication-competent retroviral vectors (RCRVs).

The invention provides a method of producing a recombinant retrovirus capable of infecting a target cell comprising transfecting a suitable host cell with the following: a vector comprising a polynucleotide sequence encoding a viral gag, a viral pol and a viral env, wherein the vector contains a cloning site for introduction of a heterologous gene, operably linked to a regulatory nucleic acid sequence, and recovering the recombinant virus. An illustration of the individual vectors used in the method of the invention is shown in FIGS. 1 and 2.

The retrovirus and methods of the invention provide a replication competent retrovirus that does not require helper virus or additional nucleic acid sequence or proteins in order to propagate and produce virion. For example, the nucleic acid sequences of the retrovirus of the present invention encode, for example, a group specific antigen and reverse transcriptase, (and integrase and protease-enzymes necessary for maturation and reverse transcription), respectively, as discussed above. The viral gag and pol can be derived from a lentivirus, such as HIV or an oncovirus such as MoMLV. In addition, the nucleic acid genome of the retrovirus of the present invention includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

Unlike recombinant retroviruses produced by standard methods in the art that are defective and require assistance in order to produce infectious vector particles, the present invention provides a retrovirus that is replication-competent.

In another embodiment, the present invention provides retroviral vectors that are targeted using regulatory sequences. Cell- or tissue-specific regulatory sequences (e.g., promoters) can be utilized to target expression of gene sequences in specific cell populations. Suitable mammalian and viral promoters for the present invention are available in the art. Accordingly, in one embodiment, the present invention provides a retrovirus having tissue-specific promoter elements at the 5' and 3' end of the retroviral genome. Preferably, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline). Transcription control sequences of the present invention can also include naturally occurring transcription control sequences naturally associated with a gene encoding a superantigen, a cytokine or a chemokine of the present invention.

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the present invention typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the present invention. For example, promoters that are active in a variety of central nervous system (CNS) neurons may be therapeutically useful in protecting against damage due to stroke, which may effect any of a number of different regions of the brain. Accordingly, the tissue-specific regulatory elements used in the present invention, have applicability to regulation of the heterologous proteins as well as a applicability as a targeting polynucleotide sequence in the present retroviral vectors.

Tissue-specific promoters may be derived, for example, from promoter regions of genes that are differentially expressed in different tissues. For example, a variety of promoters have been identified which are suitable for up regulating expression in cardiac tissue. Included, for example, are the cardiac α-myosin heavy chain (AMHC) promoter and the cardiac α-actin promoter. Other examples of tissue-specific regulatory elements include, tissue-specific promoters, such as milk-specific (whey), pancreatic (insulin or elastase), actin promoter in smooth muscle cells or neuronal (myelin basic protein) promoters. Through the use of promoters, such as milk-specific promoters, recombinant retroviruses may be isolated directly from the biological fluid of the progeny.

In addition, numerous gene therapy methods, that take advantage of retroviral vectors, for treating a wide variety of diseases are well-known in the art (see, e.g., U.S. Pat. Nos. 4,405,712 and 4,650,764; Friedmann, 1989, *Science,* 244: 1275-1281; Mulligan, 1993, *Science,* 260:926-932, R. Crystal, 1995, *Science* 270:404-410, each of which are incorporated herein by reference in their entirety). An increasing number of these methods are currently being applied in human clinical trials (Morgan, R., 1993, *BioPharm,* 6(1):32-35; see also *The Development of Human Gene Therapy,* Theodore Friedmann, Ed., Cold Spring Harbor Laboratory Press, Cold Spring Harbor, N.Y., 1999. ISBN 0-87969-528-5, which is incorporated herein by reference in its entirety). The safety of these currently available gene therapy protocols can be substantially increased by using retroviral vectors of the present invention. For example, where the retroviral vector infects a non-targeted cell, the retroviral genome will integrate but will not be transcribed. However, when the retroviral vector containing a tissue specific regulatory element infects a targeted cell the active tissue specific promoter will result in transcription and translation of the viral genome.

The phrase "non-dividing" cell refers to a cell that does not go through mitosis. Non-dividing cells may be blocked at any point in the cell cycle, (e.g., $G_0/G_1$, $G_1/S$, $G_2/M$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector of the invention is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives. For dividing cells onco-retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC) or blood neoplasia. Also included are carcinoma's of the regional lymph nodes including cervical lymph nodes, prelaryngeal lymph nodes, pulmonary juxtaesophageal lymph nodes and submandibular lymph nodes (*Harrison's Principles of Internal Medicine* (eds., Isselbacher, et al., McGraw-Hill, Inc., 13th Edition, pp1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer and ovarian cancer.

The present invention also provides gene therapy for the treatment of cell proliferative disorders. Such therapy would achieve its therapeutic effect by introduction of an appropriate therapeutic polynucleotide sequence (e.g., antisense, ribozymes, suicide genes), into cells of subject having the proliferative disorder. Delivery of polynucleotide constructs can be achieved using the recombinant retroviral vector of the present invention, particularly if ti si based on MLV, which will is capable of infecting dividing cells.

In addition, the therapeutic methods (e.g., the gene therapy or gene delivery methods) as described herein can be performed in vivo or ex vivo. It may be preferable to remove the majority of a tumor prior to gene therapy, for example surgically or by radiation.

Thus, the invention provides a recombinant retrovirus capable of infecting a non-dividing cell, a dividing cell or a neoplastic cell comprising a viral GAG; a viral POL; a viral ENV; a heterologous nucleic acid sequence operably linked to a regulatory nucleic acid sequence; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the invention may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion, depending on the packaging cell line chosen (e.g., VIF).

The invention also provides a method of nucleic acid transfer to a target cell to provide expression of a particular nucleic acid sequence (e.g., a heterologous sequence). Therefore, in another embodiment, the invention provides a method for introduction and expression of a heterologous nucleic acid sequence in a target cell comprising infecting the target cell with the recombinant virus of the invention and expressing the heterologous nucleic acid sequence in the target cell. As mentioned above, the target cell can be any cell type including dividing, non-dividing, neoplastic, immortalized, modified and other cell types recognized by those of skill in the art, so long as they are capable of infection by a retrovirus.

It may be desirable to modulate the expression of a gene in a cell by the introduction of a nucleic acid sequence (e.g., the heterologous nucleic acid sequence) by the method of the invention, wherein the nucleic acid sequence give rise, for example, to an antisense or ribozyme molecule. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, *Anal.Biochem.*, 172:289, 1988).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Of particular interest are the blocking of genes associated with cell-proliferative disorders. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

It may be desirable to transfer a nucleic acid encoding a biological response modifier. Included in this category are immunopotentiating agents including nucleic acids encoding a number of the cytokines classified as "-interleukins". These include, for example, interleukins 1 through 12. Also included in this category, although not necessarily working according to the same mechanisms, are interferons, and in particular gamma interferon (γ-IFN), tumor necrosis factor (TNF) and granulocyte-macrophage-colony stimulating factor (GM-CSF). Other polypeptides include, for example, angiogenic factors and anti-angiogenic factors. It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific target cells.

The recombinant retrovirus of the invention can be used for the treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor, (NGF), might be used to prevent degeneration of cholinergic neurons that might otherwise die without treatment. Alternatively, cells be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant retrovirus of the invention containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuronal cell and implanted into the hippocampal region of the brain.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a retrovirus for infection of a muscle or liver cell.

The present invention also provides gene therapy for the treatment of cell proliferative or immunologic disorders. Such therapy would achieve its therapeutic effect by introduction of an antisense or dominant negative encoding polynucleotide into cells having the proliferative disorder, wherein the polynucleotide binds to and prevents translation or expression of a gene associated with a cell-proliferative disorder. Delivery of heterologous nucleic acids useful in treating or modulating a cell proliferative disorder (e.g., antisense polynucleotides) can be achieved using a recombinant retroviral vector of the present invention.

In addition, the present invention provides polynucleotide sequence encoding a recombinant retroviral vector of the present invention. The polynucleotide sequence can be incorporated into various viral particles. For example, various viral vectors which can be utilized for gene therapy include adenovirus, herpes virus, vaccinia, or, preferably, an RNA virus such as a retrovirus. The retroviral vector can be a derivative of a murine, simian or human retrovirus. Examples of retroviral vectors in which a foreign gene (e.g., a heterologous polynucleotide sequence) can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). All of these vectors can transfer or incorporate a gene for a selectable marker so that transduced cells can be identified and generated. By inserting a heterologous sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Targeting is accomplished by using an antibody or ligand to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the heterologous polynucleotide. In addition, the retroviral vector can be targeted to a cell by utilizing a cell- or tissue-specific regulatory element contained in the LTR of the retroviral genome. Preferably the cell- or tissue-specific regulatory element is in the U3 region of the LTRs. In this way, after integration into a cell, the retroviral genome will only be expressed in cells where the cell- or tissue-specific promoter is active.

Alternatively, NIH 3T3 or other tissue culture cells can be directly transfected with plasmids encoding the retroviral genome, by conventional calcium phosphate transfection. The resulting cells release the retroviral vector into the culture medium.

In another embodiment, the invention provides a method of treating a subject having a cell proliferative disorder. The subject can be any mammal, and is preferably a human. The subject is contacted with a recombinant replication competent retroviral vector of the present invention. The contacting can be in vivo or ex vivo. Methods of administering the retroviral vector of the invention are known in the art and include, for example, systemic administration, topical administration, intraperitoneal administration, intra-muscular administration, as well as administration directly at the site of a tumor or cell-proliferative disorder and other routes of administration known in the art.

Thus, the invention includes various pharmaceutical compositions useful for treating a cell proliferative disorder. The pharmaceutical compositions according to the invention are prepared by bringing a retroviral vector containing a heterologous polynucleotide sequence useful in treating or modulating a cell proliferative disorder according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405-1412, 1461-1487 (1975) and *The National Formulary XIV.,* 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

For example, and not by way of limitation, a retroviral vector useful in treating a cell proliferative disorder will include a chimeric target specific ENV protein directed to a cell type of interest (e.g., one having a cell proliferative disorder), GAG, and POL proteins, a cell-specific promoter sequence in the U3 region of the LTR of the retroviral genome associated with a growth regulatory gene (e.g., probasin or HER2), and all cis-acting sequence necessary for replication, packaging and integration of the retroviral genome into the target cell. The heterologous sequence can be, for example, an antisense molecule or a suicide protein that results in the death of a cell where the retroviral genome is actively transcribed.

The following Examples are intended to illustrate, but not to limit the invention. While such Examples are typical of those that might be used, other procedures known to those skilled in the art may alternatively be utilized.

EXAMPLES

Example 1

Construction of Replication Competent Retroviruses

There have been few reports in the literature regarding the stability of insertions in the context of replication-competent MoMLV, and all of these have used insertion positions within the 3' long terminal repeat sequence (LTR). Most of these insertions were deleted within one or two serial passages of the virus. In this case the size and nature of the inserted sequences seemed to have little correlation with the stability of the vector, as small inserts were often deleted just as quickly as larger inserts. One important consideration may be the positioning of the insertion; as the reverse transcription process entails duplication of the U3 region of the 3' LTR (FIG. 1), this may result in decreased stability of non-essential sequences inserted into this position.

An infectious Mo-MLV proviral clone was excised with NheI from plasmid pZAP and ligated to the plasmid backbone of retroviral vector gIZIN. The IRES of encephalomyocarditis virus was amplified by PCR from plasmid pEMCF and appended at its 3' end to a polylinker by overlap-extension PCR. Plasmids gIZIN and pEMC-F were kindly provided by J. J. Hwang, University of Southern California. All PCR reactions were carried out with Pfu DNA polymerase (Stratagene). The IRES-polylinker was then introduced into the Mo-MLV clone at the 3' terminus of the env gene by overlap extension PCR. The resulting plasmid was termed g1ZD. The GFP gene of plasmid pEGFP-N1 (Clontech) was amplified by PCR and inserted into the multiple cloning site of g1ZD, producing g1ZD-GFP. The hygromycin phosphotransferase gene of plasmid pTK-hygro (Clontech) was similarly introduced into g1ZD to produce g1ZD-hygro. The prefix p is omitted in the designation of the viruses derived from these plasmids.

Insertion of a transgene into a less sensitive position, and in fact linking expression of the inserted transgene to viral coding sequences, might enhance the stability of the vector. Accordingly, an IRES sequence was inserted just downstream from the envelope message but upstream from the 3' LTR (FIG. 2). An IRES derived from encephalomyocarditis virus (EMCV) and a multiple cloning site were inserted just 3' of the envelope gene in a replication-competent MoMLV provirus clone, g1ZD (wild type MoMLV, see FIG. 1). The g1ZD strain of MoMLV virus is ecotropic (i.e., encoated by an envelope with murine-specific binding tropism). This particular insert position was chosen because 1) the packaging signal is known to extend past the ATG of the gag gene, thus positioning a transgene just upstream of the gag gene would greatly impair packaging efficiency, 2) the gag and pol coding sequences are initially translated as a single polypeptide which is then cleaved, thus positioning a transgene between these coding sequences would greatly impair proteolytic processing, 3) the 3' end of the pol gene actually overlaps with the 5' end of the env gene, and this overlap region contains a splice acceptor for the env transcript, thus transgene insertions into this region would be problematic, and 4) the positioning of the insert outside of the major intron ensures the insert's presence on both spliced and unspliced viral RNAs and therefore the translation of the insert from both spliced and unspliced RNAs.

The resultant construct was designated g1ZD. The multiple cloning site in g1ZD was then used to insert transgene coding sequences. The multiple cloning site in the gIZD was then used to insert transgene coding sequences. Initially maker genes such as the green fluorescent protein (GFP) gene, puromycine-resistance (puro$^R$) gene, and hygromycine-resistance (hygro$^R$) gene were inserted at this site. Suicide genes, such as the Herpes simplex virus thymidine kinase (HSV-tk) gene and the *E. Coli* purine nucleotide phosphorylase (PNP) gene, can be inserted in place of the marker genes. As the transgenes are of various sizes, resulting in IRES+transgene cassette insertions raging from 1170 bp to 1700 bp in size, it can be determined whether the inset size has an effect on the stability of the virus genome (normally 8.3 kb in size), and what the packaging limit for MoMLV might be in this context. There have been few reports in the literature regarding the stability of insertions in the context of replication-competent MoMLV, and none, that the inventors are aware of, using an IRES sequence to direct transgene expression in replication-competent vectors. This construct design greatly improves functional and genetic stability of the transgene.

The gIZD-derived replication-competent retrovirus (RCR) vectors were first tested for their ability to efficiently replicate and spread in culture. NIH3T3 and 293T cell were cultivated in Dulbecco's Modified Eagle Medium with 10% fetal bovine serum. Vector stock was produced by transfection of the vector-encoding plasmids into 293T cells using calcium phosphate-precipitation as described previously. Twenty-four hours post-transfection, the medium was replaced with fresh medium, and one day later the vector-containing supernatant was collected, filtered through a 0.45 µm filter and used immediately or frozen for later use. After initial transfection of the RCR vector plasmids into 293 cells to produce a viral stock, a 1000-fold dilution of the virus preparation was used to infect fresh plates of NIH3T3 cells. The cells were grown to confluence, the RCR-containing cell culture supernatant was harvested to assay reverse transcriptase (RT) activity, and the cells were then passaged. This cycle was repeated several times as each set of passaged cells again attained confluence.

Figure 3A:
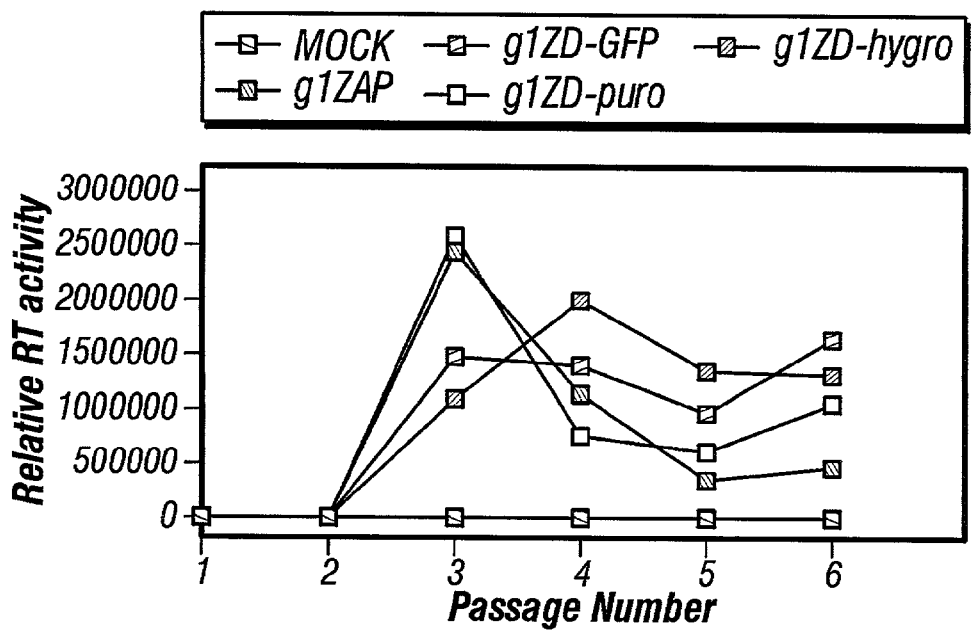
FIGS. 3A and 3B are graphs depicting a reverse transcriptase assay of MoMLV-based RCR vectors spread through NIH3T3 cells in culture. Mock=uninfected negative control; gIZAP=wild type replication-competent MoMLV virus; gIZD-gfp=replication-competent MoMLV virus with internal ribosome entry site IRES at 3' end of envelope gene and green fluorescent protein (GFP) transgene; gIZD-puro=replication-competent MoMLV virus with IRES at 3' end of envelope gene and puromycin resistance (PURO$^R$) transgene; gIZD-hygro=replication-competent MOMLV virus with IRES at 3' end of envelope gene and hygromycin resistance (HYGRO$^R$) transgene.
Figure 3B:
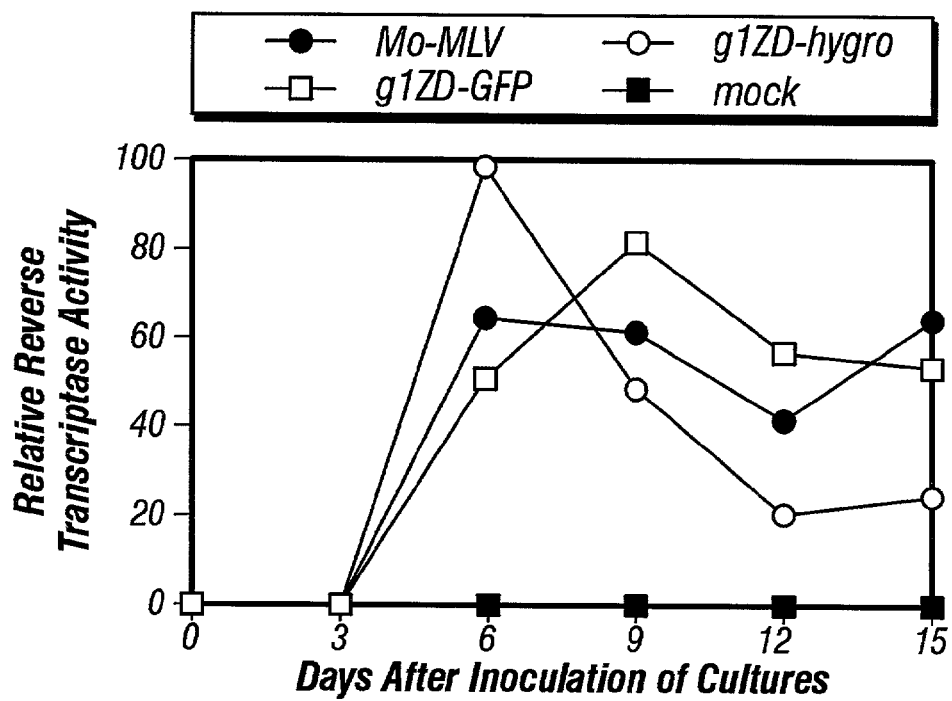

Dilutions of vector stocks were used to infect 20% confluent NIH3T3 cells. Every 3 days for the following 2 weeks, the supernatant was collected and the cells were split 1:4. To quantitate reverse transcriptase activity, an aliquot of each supernatant was incubated at 37° C. for one hour in a cocktail containing ($^{32}$P)dTTP, poly(rA) template, and oligo-dT primers. RT activity was quantified using poly-riboA template and an oligo-dT primer for incorporation of radiolabeled dTTP, and the reaction products were spotted on nitrocellulose and radioactivity measured by PhosphoImager. The time course of RT activities over several passages shows a classic peak and plateau pattern, thus indicating that all gIZD-derived RCR vectors carrying marker genes are capable of efficient replication and spread throughout a cell culture at levels comparable to wild-type virus (FIG. 3). Thus, even relatively large insertions, that stretch the packaging capacity of MoMLV to its limit, do not appear to impair the replicative ability of the virus.

Figure 4:
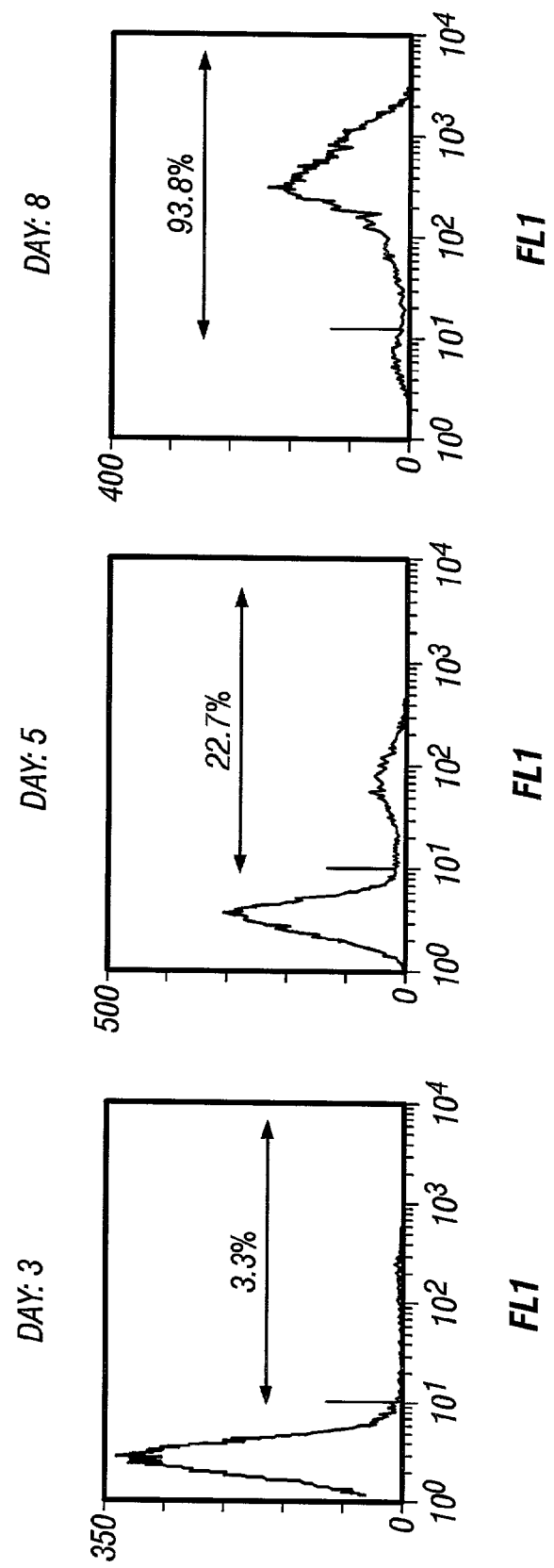
FIG. 4 are graphs showing fluorescence-activated cell sorter (FACS) analysis of GFP expression from gIZD-gfp RCR vector spread at various time points (Day 3, Day 5, and Day 8) after initial infection.
Figure 6B:
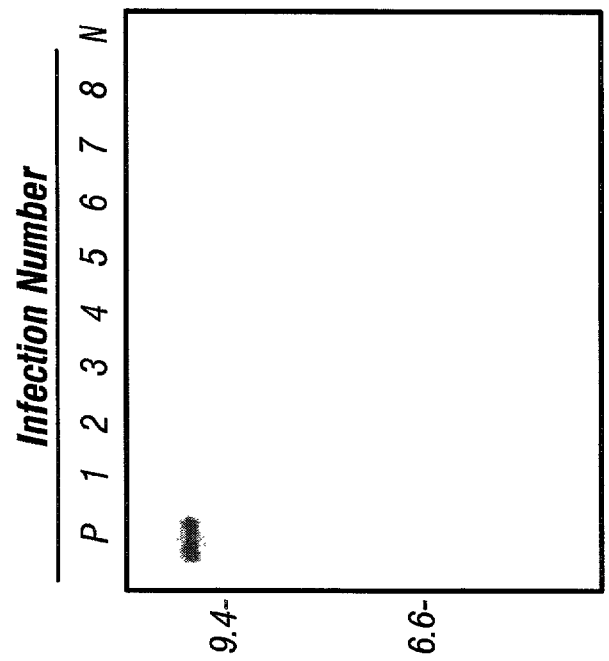
FIG. 6 is a gel photo showing the stability of the replication-competent gIZD-GFP vector over multiple serial passages. Lane P is a control sample containing either g1ZD-GFP (A) or g1ZD-hygro (B) plasmid DNA digested with NheI. The other lane numbers denote the serial passage number. (A) DNA from cells infected with g1ZD-GFP probed with the GFP cDNA (left), and with the LTR-gag fragment (right). (B) DNA from cells infected with g1ZD-hygro probed with the hygromycin resistance gene (left), and with the LTR-gag fragment (right). Intact, full length gIZD-GFP is observed up to at least passage no. 11 (A, B). As shorter deletion mutant appears in passage nos/7-8 which then becomes the dominant form. N denotes lanes containing Hirt DNA isolated from uninfected NIH3T3 cells.
Figure 6B:
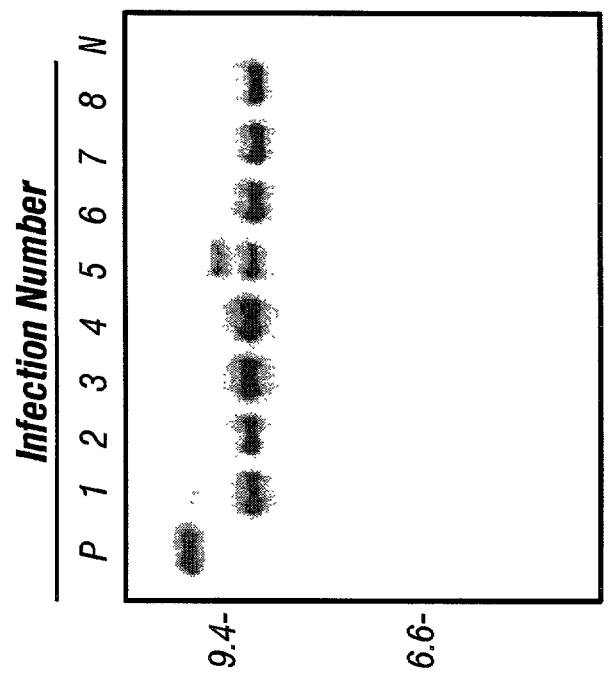

The gIZD-derived RCR vector containing GFP as the marker gene (gIZD-GFP) was used to follow transgene expression over time as the virus spread through the NIH3T3 cell culture. The GFP marker can be detected by fluorescence-activated cell sorter (FACS) analysis, using the same wavelength as that used for detection of fluorescein (FITC; cannel FL1). NIH3T3 cells were washed with phosphate buffered saline (PBS), trypsinized and collected by low-speed centrifugation. Cells were resuspended in PBS at approximately 10$^5$ cells/ml and analyzed for fluorescence with a Becton Dickinson FACScan using a fluorescein isothiocyanate filter set. These results show that initial transduction levels at high dilution of the virus stock are extremely low (about 3%) at Day 3, but expression in the culture rapidly increased over time, as seen by the shifted peak of mean fluorescence, so that by Day 8 almost 100% of the culture is now expressing GFP (FIG. 4). Thus, this indicates that transgene expression is not lost as the RCR vector spreads through the cell culture, and in fact the transgene is efficiently delivered to practically all of the cells even with low initial transduction levels (FIGS. 5 and 6).

Example 2

Construction of RCR Vectors Targeted to Human Breast Cancer Cells

Figure 2B:
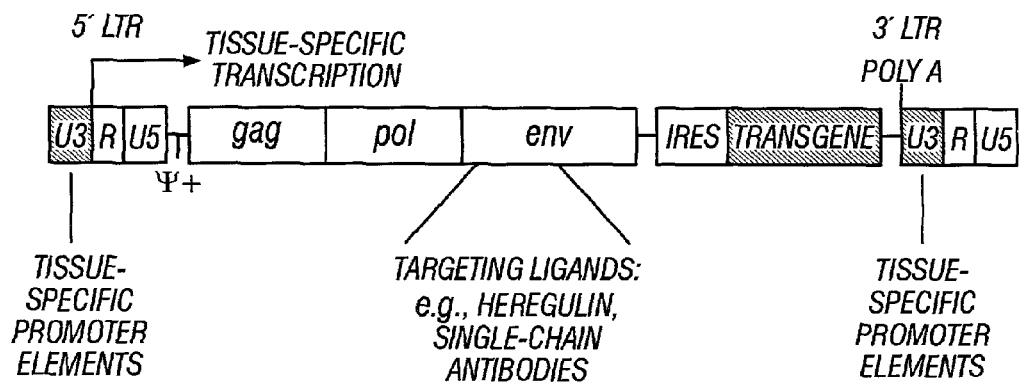

Chimeric MoMLV and SNV env sequences which contain targeting moieties directed against human breast cancer cells, and which have proven successful for targeting in previous studies, were utilized. The targeting moiety for MoMLV env was the peptide hormone heregulin, and the targeting moiety for SNV env was the single chain antibody B6.2, originally derived by immunizing mice with a membrane-enriched fraction from a human breast tumor. Using an IRES sequence, either a marker gene (such as GFP) or a suicide gene (such as HSV-tk or PNP) is linked to the chimeric envelope construct at the 3' end. These chimeric envelope/IRES/transgene constructs are then recloned back into the replication-competent wild type forms of MoMLV or SNV, replacing the original env gene (FIG. 2b). This results in replication-competent retrovirus vectors that are targeted specifically to cancer cells.

Tumors were established by the injection of 1.5×10$^6$ NMU rat breast adenocarcinoma cells subcutaneously into the anterior flanks of 6-week-old nu/nu BALB/c mice (Simonsen Laboratories). Four weeks later, the tumors had grown to 100-150 mm$^3$, at which time they were injected with 80 µl of supernatant from g1ZD-GFP infected NIH3T3 cells, containing 1×10$^4$ PFU vector. At regular intervals thereafter, subsets of the mice were sacrificed, and their tumors were surgically removed. To produce single-cell suspensions, the entire mass of each tumor was finely minced and incubated for one hour at 37° C. in five volumes of Hank's balanced salt solution (HBSS) containing 100 U/ml collagenase IV. The dispersed cells were then washed and resuspended in PBS for flow cytometric-analysis.

Although Kasahara et al. (*Science*, 266:1373-1376 (1994)) and Chu et al. (*Journal of Virology*, 69:2659-2663 (1995)) have found that the co-expression of wild-type MoMLV envelope is usually required for proper processing and transport of chimeric MoMLV envelope constructs to the surface of the producer cells, and possible also for proper function during entry, some groups have been able to encoat virions with chimeric envelope alone by inserting the ligand sequence into the extreme amino-terminus of the MoMLV envelope. The strategy was used for construction of the heregulin/MoMLV envelope to be used in the replication-competent vectors. Furthermore, although MoMLV is the standard retrovirus used in most gene therapy protocols, SNV is advantageous for targeting due to the following characteristics: 1) its maximum packaging capacity is larger than that of MoMLV and may thus tolerate the additional sequences and genes without drastic loss of titer, 2) the SNV envelope has been found to be extremely stable, tolerating major truncations without loss of the ability to assemble properly on the packaging cell surface and it has been shown the chimeric SNV en lope constructs contain exogenous ligand sequences can be expressed without the need for wild type SNV envelope, and 3) wild type SNV is considered to be completely non-pathogenic for humans (Bacus et al., *Am. J. Clin. Pathol.*, 102:S13-24 (1994)).

Example 3

Creation of RCR Vector-producing Cell Lines

The above MoMLV and SNV genomic constructs are transfected into human breast cancer cell line MD-MB-453 (ATCC accession umber HTB 131), which expresses high levels of HER-2 and HER-4 (Krause et al., *EMBO Journal*, 6:605-610 (1987)). The constructs which contain the GFP marker gene are transfected first, as the presence of the marker gene enables us to monitor the transfection efficiency by FACS analysis. After transfection, the targeted RCR vectors produced by the primary transfectants are capable of horizontal infection of adjacent cells not initially transfected, by biding via the heregulin or B6.2 single-chain antibody moieties. This can be detected as an increasing percentage of GFP-positive cells over time. Furthermore, the cell culture medium should contain supernatant virus, which can infect and transduce fresh cultures of MDA-MB-453 cells. The GFP-containing vectors thus enable one to determine the time course of transfection and infection events, and rate of virus spread through the human breast cancer cell culture. Based on this information, similar studies are performed with the HSV-tk- and PNP-containing vectors, and in this case transduction is monitored by Southern blot or quantitative PCR for integrated vector sequences. The HSV-tk and PNP transgenes are also functionally tested by determining whether sensitivity had been conferred to the prodrugs ganciclovir and 6-methyl purine-deoxyriboside, respectively.

Example 4

Testing of Tissue Specificity of the Virus in Culture

Cell culture medium from virus-producing MDA-MB-453 cells is used to infect a variety of human target cells, in order to ascertain the tissue-specificity of the virus vectors. As negative control virus, the target cells are exposed to wild type ecotropic MoMLV or SNV vectors containing the GFP marker gene, and as positive control virus, the target cells are infected with an amphotropic MoMLV vector containing GFP.

The target cells again are the human breast cancer cell line MDA-MB-453, which as noted above over expresses both HER-2 and HER-4, and as a negative control cell line, the human breast cancer cell line MDA-MB-231 (ATCC accession number HTB 26), which does not express any detectable HER-2 or HER-4 is used. No background infectivity is seen with the wild type ecotropic MoMLV or SNV vector controls; thus successful infection by the chimeric vectors depends on specific interaction between the heregulin or B6.2 single-chain antibody targeting moieties in the virus envelope and their corresponding receptor or antigen on the target cells. Other human breast cancer cell lines that are used as targets include BT474 (which over expresses both HER-2 and HER-4) and MCF7 (which only expresses HER-4). In addition, negative control cell lines which are of human origin but not derived from mammary epithelium are used to further test tissue-specificity of invention.

As noted above, infected cells are examiner by FACS analysis for GFP expression, or tested for transduction of HSV-tk or PNP by Southern blot or quantitative PCR and by exposure to ganciclovir or 6-methyl purine-deoxyriboside.

Example 5

Targeting of RCRV's by Incorporation of Tissue-specific Promoter Elements

Retroviral tropism can be re-directed by altering the transcriptional activity of the virus through replacement of regions of the viral long terminal repeat (LTR) with cell-specific promoter elements. This strategy has been used by other groups to target retroviral transcription to particular tumor cell types.

The MoMLV proviral LTR sequences consist of 3 distinct regions, designated U3, R, and U5, which are repeated at each end of the genome. The promoter elements that control transcription of the RNA genome and therefore replication of the virus, reside in the U3 region. The R region contains the start site of transcription, and therefore the upstream U3 region is not included in the genomic RNA transcript. However, the transcript reads through to the U3 sequence into the 3' LTR, which also contains polyadenylation signals, and the 3' LTR U3 region is re-duplicated at the 5' end during the process of reverse transcription. Thus, for alterations in the LTR promoter to be permanent over serial cycles of replication, the alterations is incorporated into the U3 region of the 3' LTR.

In the present invention tissue specific elements are incorporated in the LTR 3' U3 region in order to target RCR vector replication. As a practical example, transcription targeting to prostate cancer cells is shown. Using the specificity of transactivating prostate-specific elements which interact with cis-acting promoter sequences (androgen response elements) investigators have been able to achieve tissue-specific transgenic targeting of oncogenic proteins (Greenberg et al., *Proc Natl. Acad. Sci. USA*, 92:3439-43 (1995); and Garabedian et al., *Proc. Natl. Acad. Sci USA*, 95:15382-7 (1998)). One of the most well-characterized proteins uniquely produced by the prostate and regulated by promoter sequences responding to prostate-specific signals, is the rat probasin protein. Study of the probasin promoter region has identified tissue-specific transcriptional regulation sites, and has yielded a useful promoter sequence for tissue-specific gene expression. The probasin promoter sequence containing bases −426 to +28 of the 5' untranslated region, has been extensively studied in CAT reporter gene assays (Rennie et al., *Mol Endo,* 7:23-36 (1993)). Prostate-specific expression in transgenic mouse models using the probasin promoter has been reported (Greenberg et al., *Mol Endo,* 8:230-9 (1994)). Gene expression levels in these models parallel the sexual maturation of the animals with 70 fold increased gene expression found at the time of puberty (2-6 weeks). Castration of the animals will drop gene expression to near zero which can be increased to pre-castrate levels following the parenteral administration of testosterone. The probasin promoter (−426 to +28) has been used to establish the prostate cancer transgenic mouse model that uses the fused probasin promoter-simian virus 40 large T antigen gene for targeted over expression in the prostate of stable transgenic lines (Greenberg et al., *Proc Natl. Acad. Sci. USA,* 92:3439-43 (1995)). Thus, this region of the probasin promoter is incorporated into the 3' LTR U3 region of the RCR vectors. Thus providing a replication-competent MoMLV vector targeted by tissue-specific promoter elements.

Example 6

Incorporation of Prostate-specific Promoter Elements in to the RCRV LTR

Figure 8:
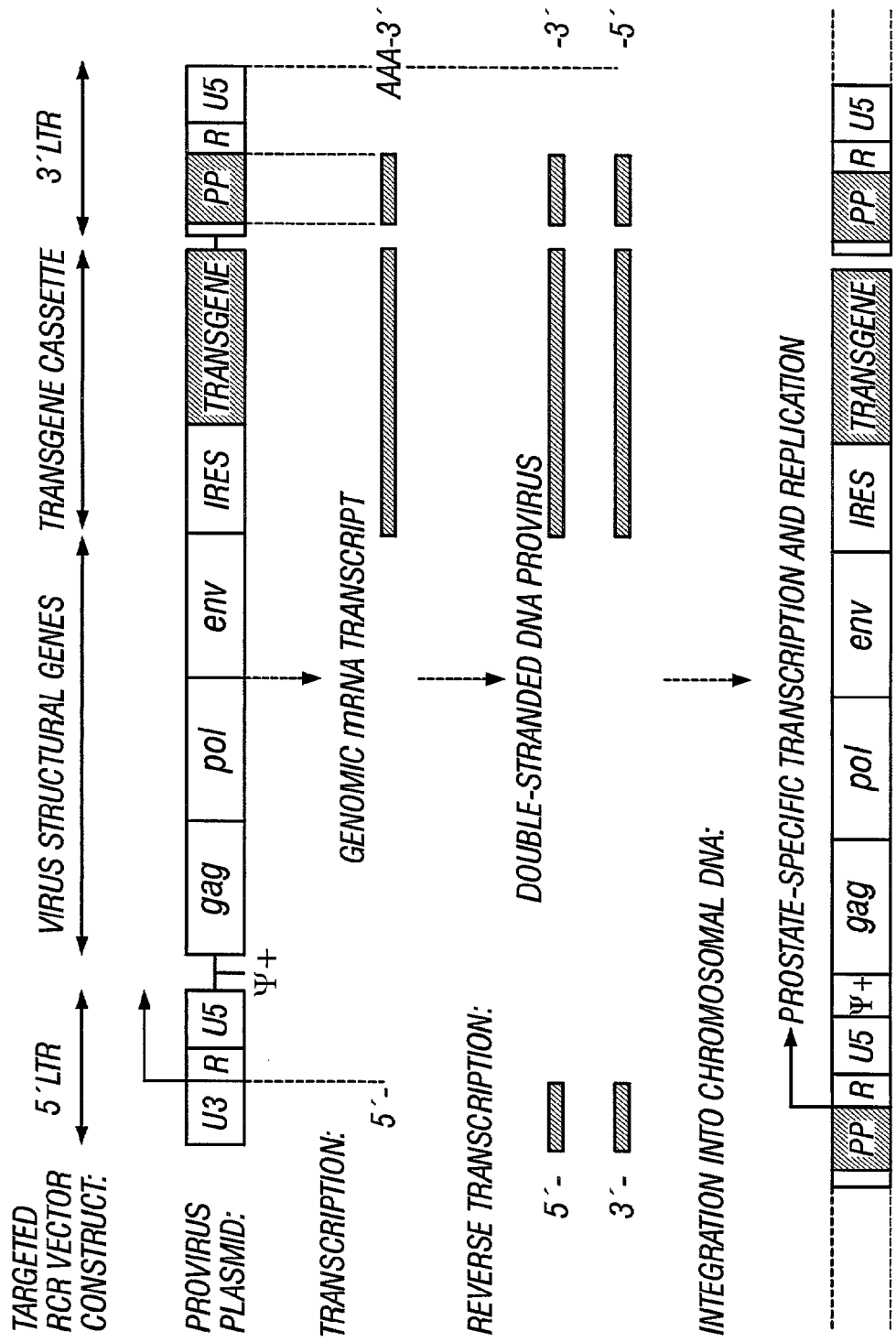
FIG. 8 is a schematic of a recombinant retroviral vector of the invention containing a probasin promoter sequence.
Figure 9A:
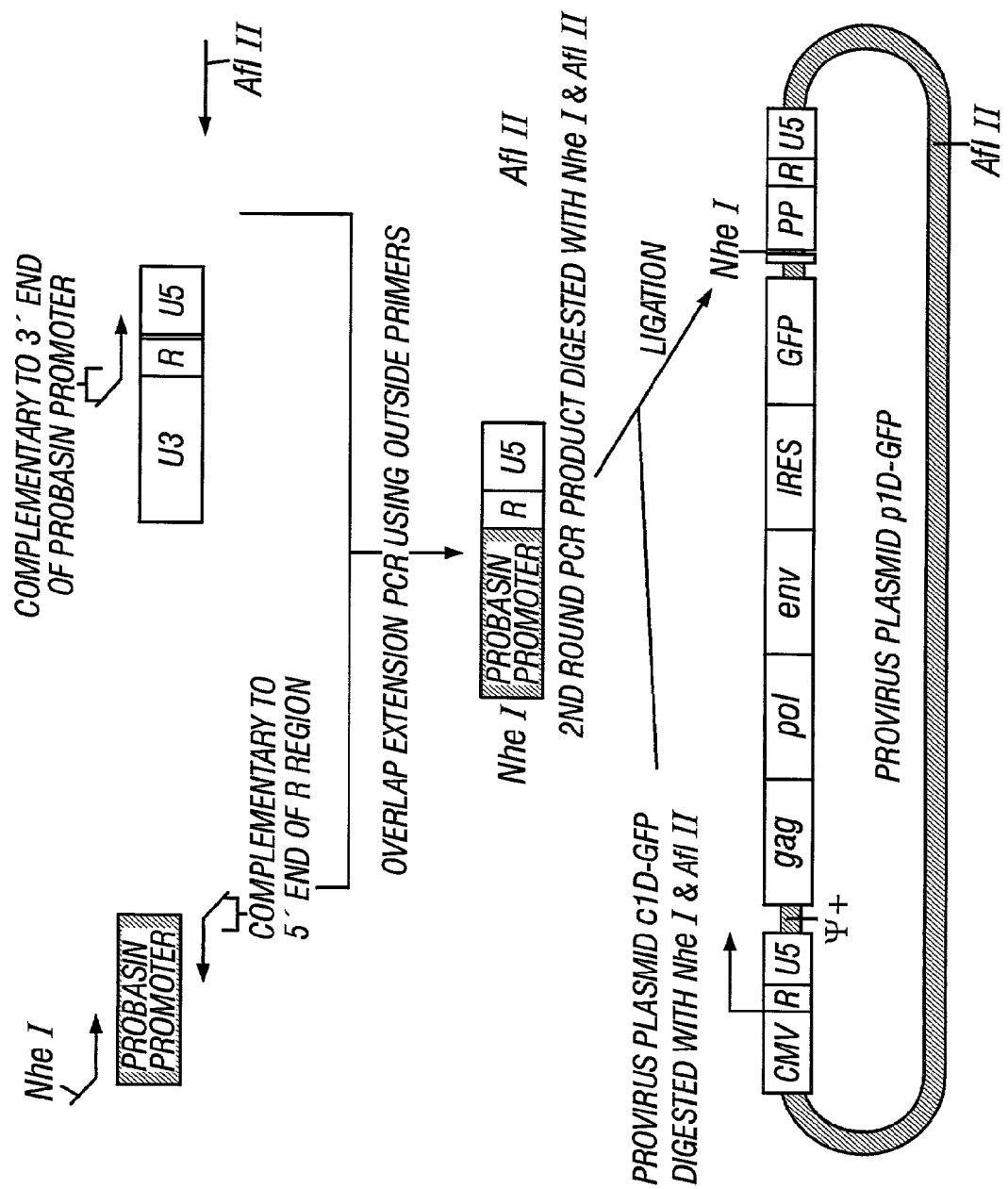
FIGS. 9A and 9B show the construction of a recombinant replication competent retrovirus of the invention targeted to prostate cancer cells.
Figure 9B:
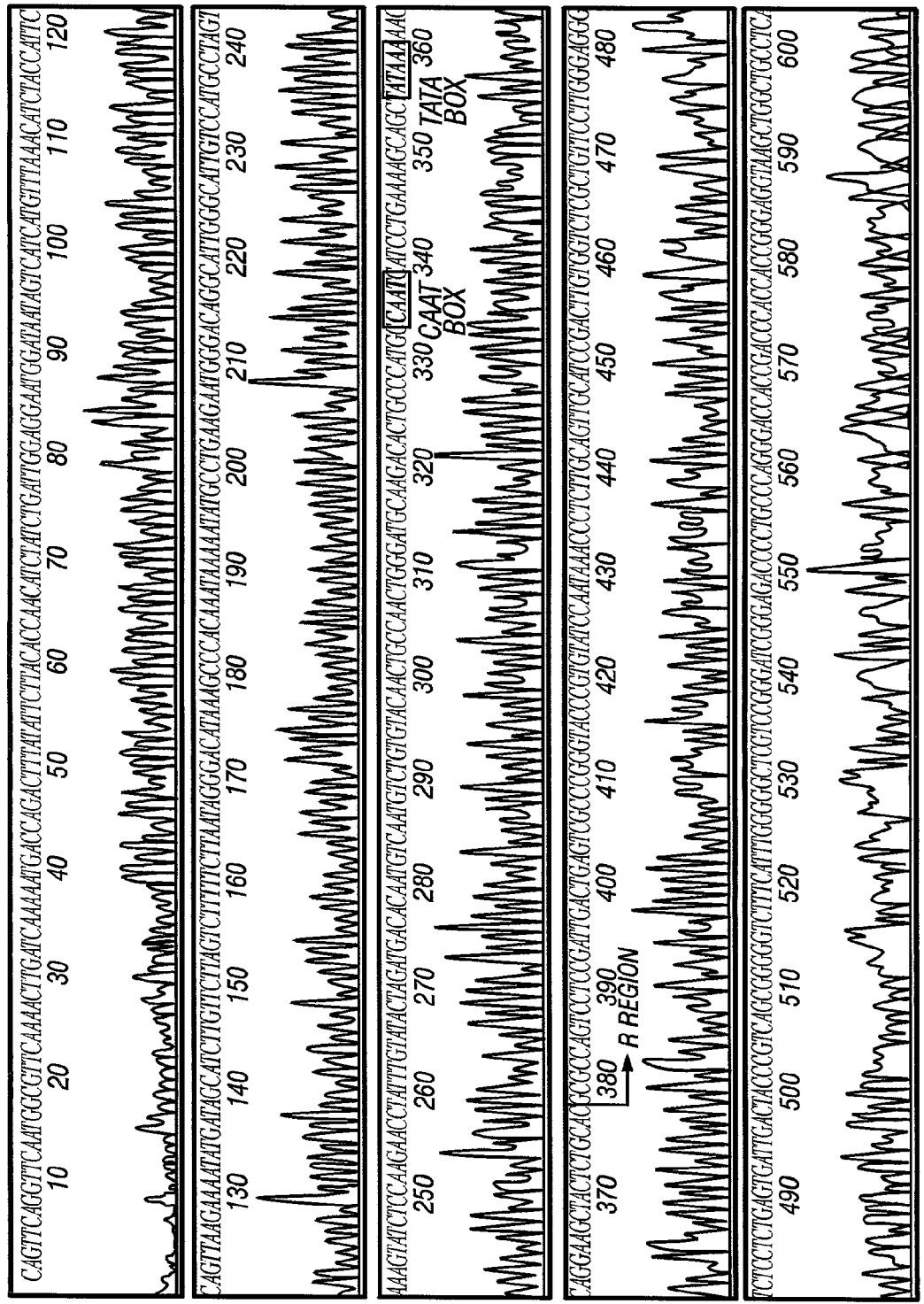

A fragment of the rat probasin androgen-sensitive promoter (from −426 to +28) that has been shown to specify prostate-specific gene expression has been engineered into the U3 region of the retroviral 3' LTR in both ecotropic and amphotropic RCR vectors. The 5' end of the U3 region is recognized by viral integrase protein and so overlap extension PCR was used to precisely place the probasin promoter just downstream of the beginning of the U3 region in the 3' LTR, replacing the rest of the U3 sequence up to the R region. Since it is initially placed downstream, this modified U3 region will not be operative upon transfection of the provirus construct into 293 cells and production of the vector transcript will proceed normally, but after a single round of replication the probasin sequence will be re-duplicated in the U3 region of the 5' LTR (FIG. 8), and thereafter should specify prostate cell-specific replication of the virus. Probasin-targeted RCR vectors have been constructed containing the EMCV IRES-GFP marker gene cassette; in this case the U3 region in the 5' LTR of g1ZD-GFP was first replaced with a CMV promoter (c1ZD-GFP) to remove the Nhe I site in the 5' LTR (and also to enhance expression and titers after initial transfection in 293 cells), so that the Nhe I site in the 3' LTR is now unique, and can be used to insert the probasin promoter fragment (FIG. 9A: replacement of the 3' U3 region with the probasin promoter by overlap extension PCR; FIG. 9B: sequence of the 3' LTR in p1ZD-GFP, showing the probasin promoter/R region joint). It should be noted in this context that, although insertions of non-essential transgenes in the U3 region are indeed prone to deletion, the probasin promoter in this case will completely replace the wild type promoter elements in the viral LTR, therefore deletions of the probasin promoter would simply result in a virus that is unable to replicate, thus there would be selection pressure against such deletions. To the inventors' knowledge this would represent the first example of a replicating retroviral vector controlled by transcriptional regulation.

A fragment of the rat probasin androgen-sensitive promoter was constructed by polymerase chain reaction (PCR) amplification from genomic DNA using primers ATCCA-CAGTTCAGGTTCAATGGCG (SEQ ID NO:1) and CTGC-TACCTTCTTTTTGA (SEQ ID NO:2) GATTCTTGTCTGT-CATCATACTGG (SEQ ID NO:3). As discussed above, this is the same promoter fragment (from −426 to +28) that specifies prostate-specific oncogene expression in the probasin-SV40 T antigen transgenic mouse. A NheI-SfiI linker sequence was added to the 5' primer while an AflII site was added to the 3' end of the 3' primer. This PCR product was inserted into the pcDNA3.+expression plasmid (Invitrogen) following a NheI-AflII digestion. The presence of the probasin insert was confirmed by restriction digest with NheI-AflII to isolated the 550 bp fragment.

This probasin promoter sequence is engineered into the U3 region of the retroviral 3' LTR by overlap extension PCR in both gIZD-GFP and gIZA-GFP and also in the GIZD and gIZA vector constructs that contain the PNP or HSV-tk therapeutic genes. The 5' end of the U3 region is recognized by the viral integrase protein and,so overlap extension PCR will be used to precisely place the probasin promoter just downstream of the beginning of the U3 region in the 3' LTR, replacing the rest of the U3 sequence up to the R region. This modified U3 will not be operative upon initial transection of the RCR vector construct into 293 cells, but after one round of replication the probasin sequence will be re-duplicated in the U3 region of the 5' LTR, and thereafter should specify prostate cell-specific replication of the virus. The construct is transfected into 293 cells, and the supernatant harvested to test the cell type-specificity of viral replication, as described below.

Example 7

Figure 10:
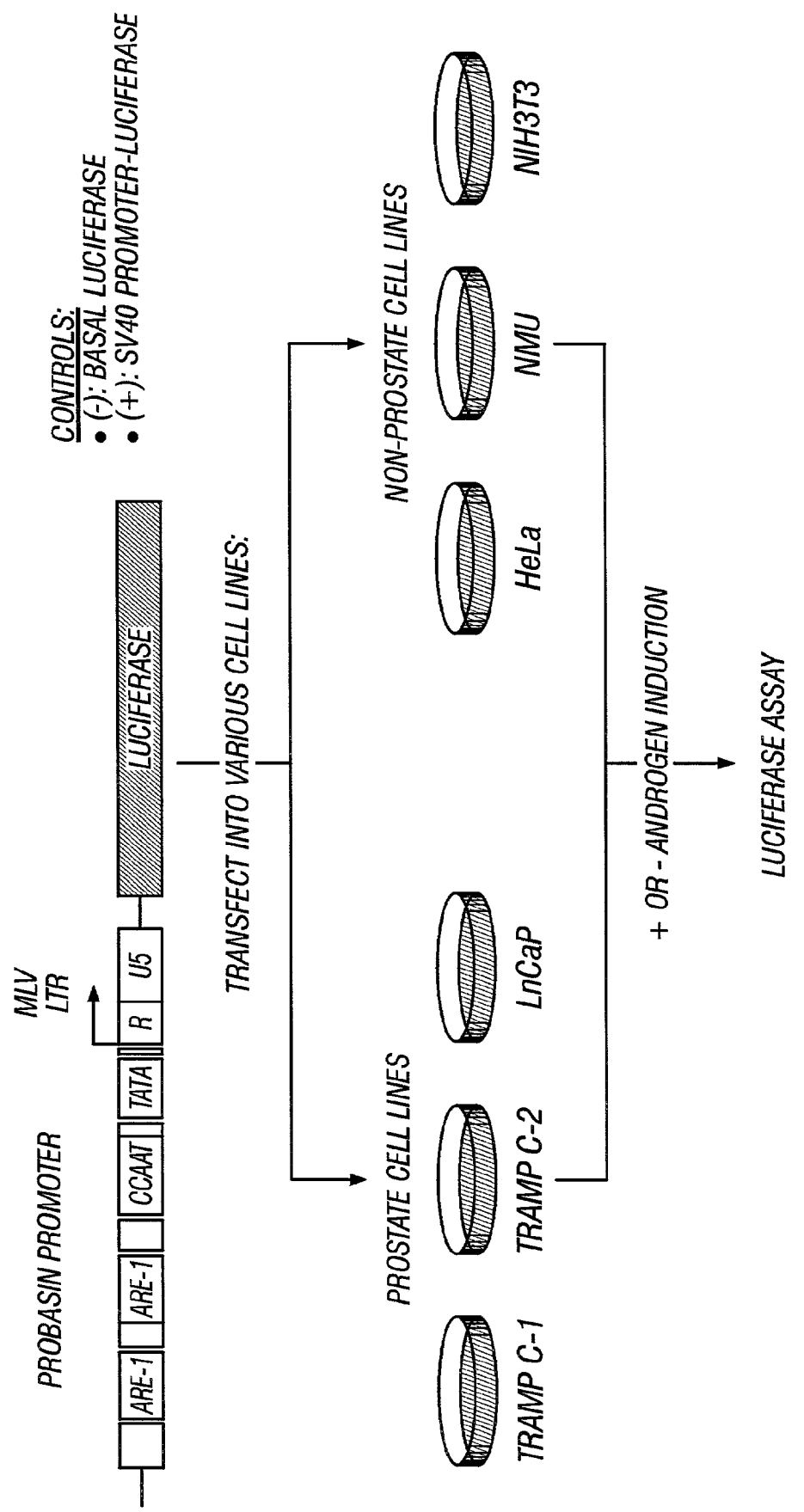
FIG. 10 depicts a strategy used for determining prostate cell-specificity and androgen-inducibility of the probasin-LTR hybrid promoter.
Figure 11:
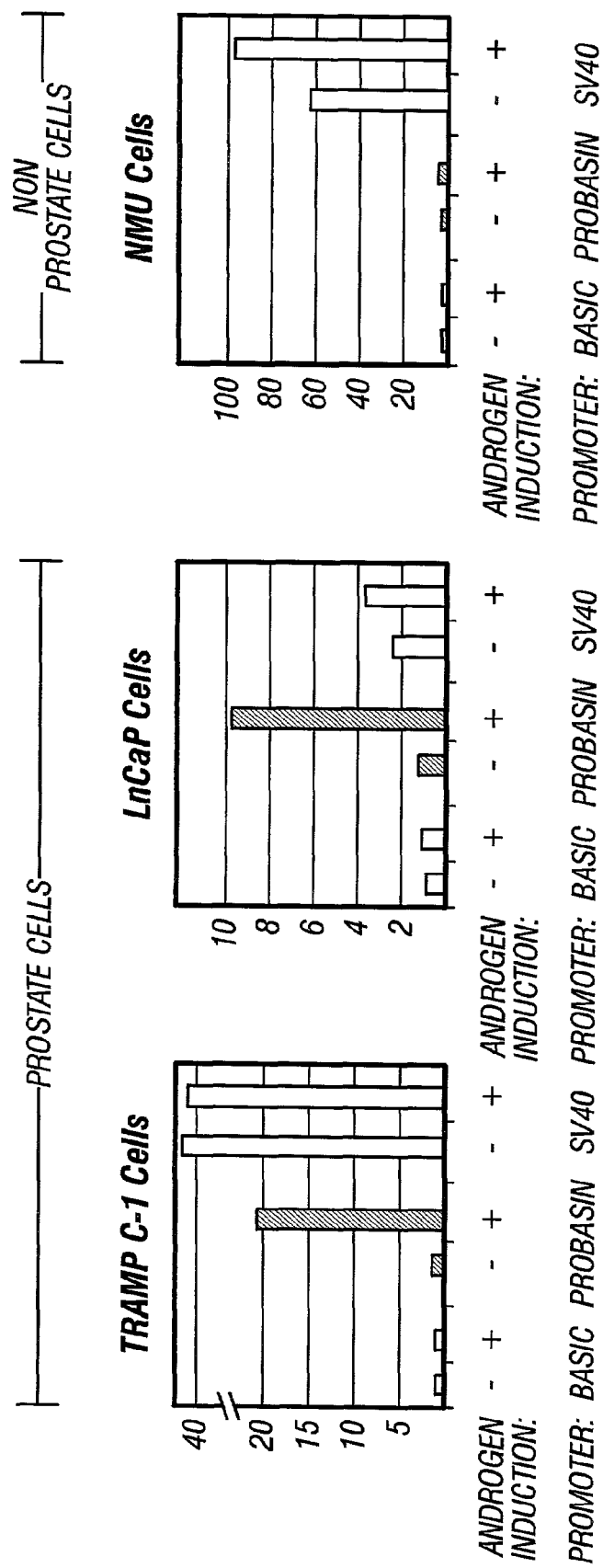
FIG. 11 shows the results of the assay depicted in FIG. 10.

Testing the Tissue Specificity of the Transcriptionally Targeted RCRV in Culture In order to confirm that the 430-bp probasin promoter would still be capable of prostate-specific, androgen-inducible expression after being incorporated into the retroviral long terminal repeat (LTR), this hybrid promoter was constructed and used to drive expression of a luciferase reporter gene. As shown in FIG. 10, this construct was tested in both prostatic and non-prostatic cell lines, in the presence and absence of androgen stimulation. A representative set of results is shown in FIG. 11; the results confirm that the probasin-LTR hybrid promoter is active with androgen stimulation only in prostate cell lines, whereas non-prostatic cell lines show little activity even in the presence of androgen stimulation. Similar results were obtained with the other cell lines tested.

Figure 12:
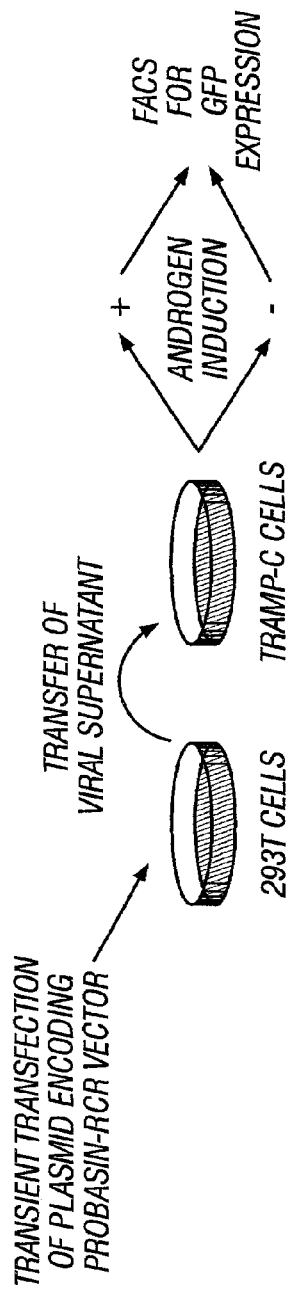
FIG. 12 depicts a strategy used for examining transcriptional regulation of RCR vectors driven by the probasin-LTR hybrid promoter.
Figure 13:
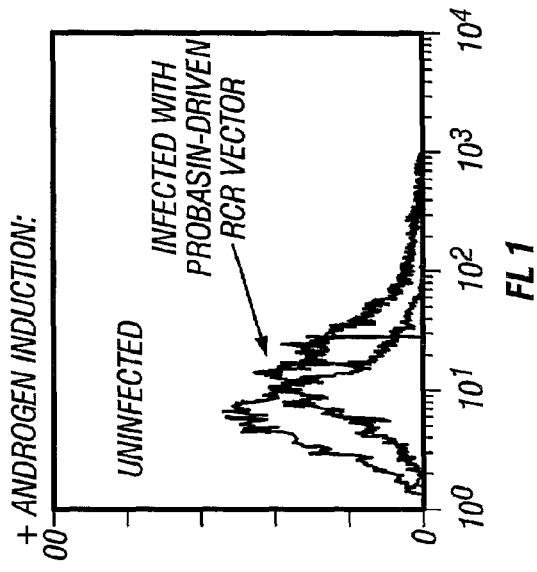
FIG. 13 shows the results of probasin-LTR driven androgen-responsive expression of the RCR vector GFP transgene after infection of TRAMP-C cells.
Figure 13:
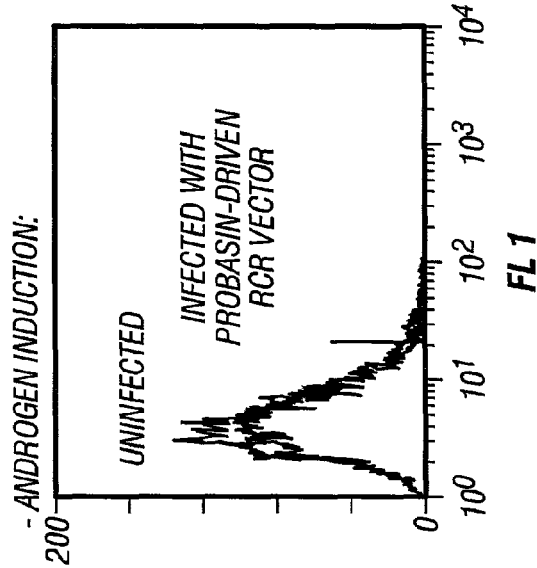

The probasin-LTR hybrid promoter was then incorporated into RCR vectors carrying the green fluorescent protein (GFP) marker gene, by replacement of the 3' LTR so that probasin-driven expression would occur only after one round of reverse transcription and re-duplication of the 3' LTR at the 5' end. As shown in FIG. 12, virus preparations were generated from these constructs by harvesting the supernatant medium 48-72 hours after transient transfection of 293T cells. These virus preparations were filtered to exclude cell debris, and then used to infect murine prostate cancer (TRAMP-C) cell lines. GFP expression in the infected TRAMP-C cells was examined by fluorescence-activated cell sorter (FACS) analysis in the presence and absence of androgen stimulation. As shown in FIG. 13, a shift in fluorescence indicating expression of the GFP marker gene occurred in the infected prostate cells only upon androgen stimulation.

In addition, the genomic constructs were used for infection of the human prostate cancer cell line LnCaP, which expresses high levels of the prostate-specific membrane antigen (PSMA) and supports high level expression of the probasin promoter. The RCR vectors which contain the GFP marker gene were used for infection first, as the presence of the marker gene will enable one to monitor the transduction efficiency by FACS analysis. After initial transduction, the targeted RCR vectors produced by the primary transfectants are capable of horizontal infection of adjacent cells not initially transfected. This is detected as an increasing percentage of GFP-positive cells over time. Furthermore, the cell culture medium will contain supernatant virus, which can infect and transduce fresh cultures of LnCaP cells. The GFP-containing vectors thus enabled determination of the time course of transfection and infection events and rate of virus spread through the prostate cancer cell culture. Based on this information, similar studies are performed with the HSV-tk- and PNP-containing suicide gene vectors, and in this case transduction is monitored by Southern blot or quantitative PCR for integrated vector sequences. The HSV-tk and PNP transgenes are also functionally tested by determining whether sensitivity is conferred to the prodrugs ganciclovir and 6-methylpurine-deoxyriboside, respectively.

Targeted RCR vectors are also used to infect a variety of non-prostatic target cells, in order to confirm the tissue-specificity of the virus vectors. As a control virus, the target cells are exposed to wild-type ecotropic or amphotropic MoMLV vectors containing the GFP marker gene.

Example 8

Transduction of Prostate Tumors in vivo

To study in vivo transduction a number of models are available that mimic the various clinical aspects of prostate cancer and include spontaneous rodent models, human xenograft systems using immunocompromised murine hosts and murine transgenic models. The Dunning R-3327 rodent model for adenocarcinoma of the prostate involves the use of subcutaneously implanted tumors in Copenhagen rats (Dunning, W., *Natl. Cancer Inst.*, 12:p351 (1963)). This model allows the study of androgen independent progression and the process of metastasis formation using the MAT-Lylu or MAT-lu sublines (Smolev et al., *Cancer Treat. Rep.*, 61, 273 (1977)).

In addition, the successful development of transgenic animal models that are capable of the spontaneous development of prostate cancers that resemble human adenocarcinomas have relied on the tissue-specific transgene expression. In particular, the probasin promoter driving the SV40 T-antigen has been used to establish a prostate cancer transgenic mouse model. This well worked out model demonstrates spontaneous prostate tumors histologically similar to those that develop in humans, although it lacks the underlying hormonal basis thought o play a central role in prostate tumor initiations. The in vivo efficacy of the transcriptionally targeted RCRV's can be shown using this model.

Male transgenic mice at puberty are monitored of the development of prostate tumors. The tumors are injected with the targeted replication-competent MoMLV or SNV vectors carrying GFP or with negative and positive control virus preparations, and transduction assessed after another two weeks. At that time, the animals are sacrificed and the tumors harvested. Tissue samples from tumors exposed to viral vectors carrying the GFP gene are snap frozen in liquid nitrogen and frozen sections examined histologically under UV fluorescence microscopy. Based on these results, similar experiments are performed using ht targeted RCR vectors carrying HSV-tk or PNP. In this case, tow weeks after the xenografts are exposed to viral vectors carrying the HSV-tk or PNP gene, ganciclovir or 6-methyl purine-deoxyriboside is administered to the animals and the extent of shrinkage of the tumors assessed. Control groups are left untreated as a control for tumor growth.

Increased transduction efficiency by the use of target-restricted, replication-competent retroviral vectors would represent a significant improvement in vector design. As the initially infected tumors cells in turn produce more virus, this strategy takes advantage of the amplification process inherent in the wild-type virus life cycle. Targeting the retrovirus specifically and exclusively to tumors cells limits and controls the replicative process, and the use of normally non-pathogenic viruses as the basis for these vectors, as well as the incorporation of suicide gene in the vectors as a "self-destruct" mechanism, provide further safeguards which minimize the risk to normal cells.

Example 9

Intra-tumoral Spread of the RCRV's in Breast Cancer Model

The in vivo application of replication-competent MoMLV vectors by intra-tumoral injection into solid tumors derived from rat NMU cells (nitrosomethylurea-induced breast cancer) in a nude mouse subcutaneous xenograft model was also performed. NMU cells are known to be tumorigenic in nude mice. Nude mice were anesthetized and a subcutaneous injection of $2\times10^6$ NMU cells in PBS suspension was performed to establish tumors. The tumors were allowed to grow to approximately 1 cm in diameter over a period of 4 weeks, at which point the g1ZD-GFP RCR vector was administered by intra-tumoral injection of 100 µl of the vector preparation.

The titer of the g1ZD-GFP vector preparation was $10^5$/ml titer by XC cell syncytia assay, therefore this constitutes a total inoculum of only $10^4$ infectious units of virus. In this instance, taking into account the tumor growth and cell division following initial establishment, a conservative estimate of the multiplicity of infection (MOI) would be on the order of at least 0.001 (and perhaps more likely to be on the order of 0.0001). Thus the initial transduction efficiency would be expected to be as low as, or lower than, 0.1%. Again, this initial inoculum of virus supernatant is comparable to the low transduction efficiencies obtained in the clinical trials using intra-tumoral injection of PA317 packaging cell lines to transduce glioblastoma.

Tumors were allowed to grow for various intervals after vector injection, and a set of mice was sacrificed and the tumors were harvested at 2 week, 4 week, and 6 week time points post-injection. After tumor harvest, the tumors were sectioned and some tumor samples were immediately frozen for subsequent isolation of genomic DNA and Southern blot analysis. The other tumor samples were minced, immediately treated with collagenase for 3-4 hours to disaggregate the tumor cells while still viable, washed and resuspended in PBS, and examined by FACS analysis the same afternoon. Thus horizontal spread of the virus vector after disaggregation of the tumor cells is unlikely to have affected the results, as there was not enough time elapsed for retroviral entry, integration, and GFP transgene expression to have occurred prior to FACS analysis.

Figure 7:
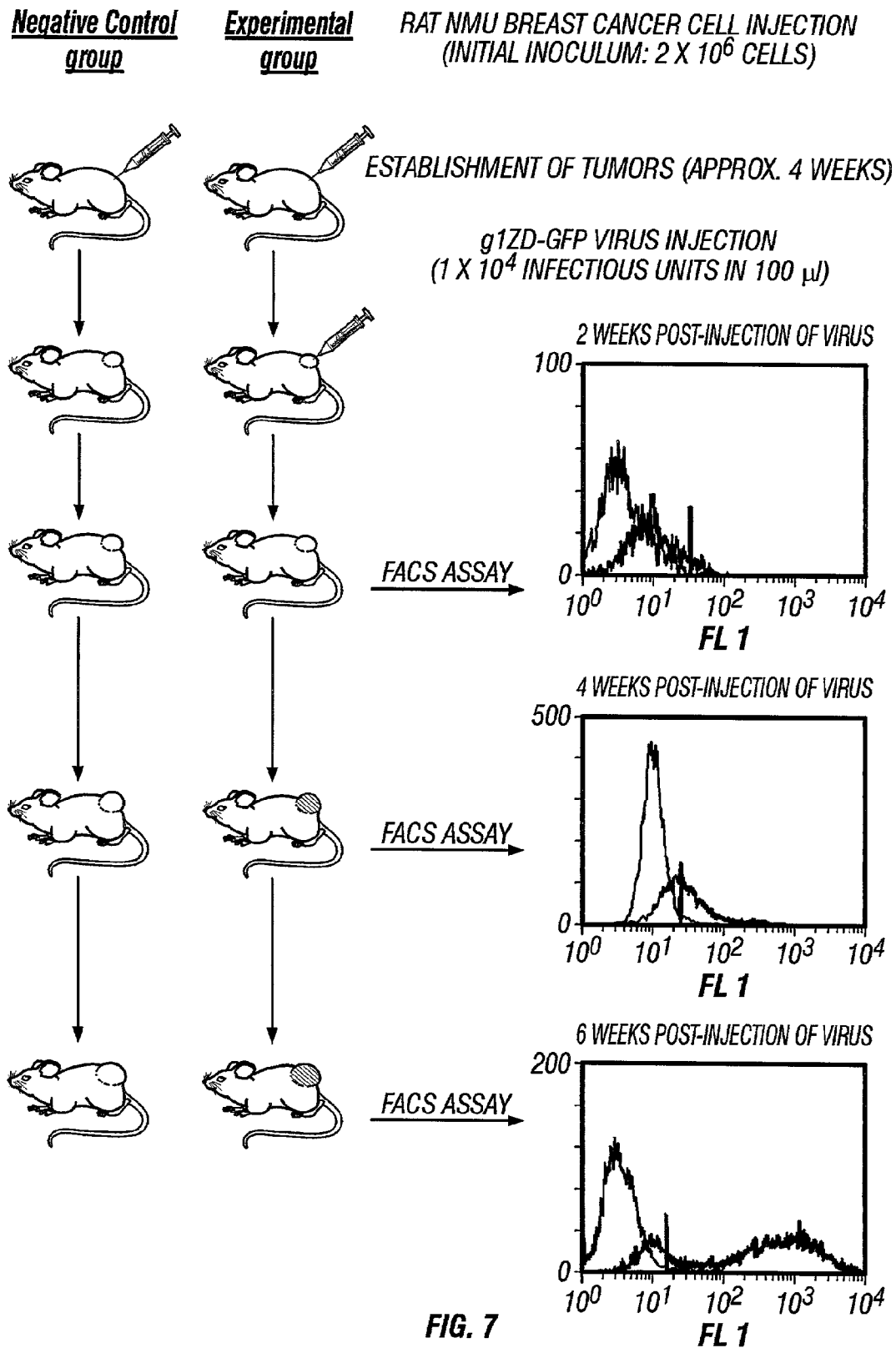
FIG. 7 is a schematic showing the experiment and results demonstrating the highly efficient intra-tumoral spread of the replication-competent gIZD-GFP vector within a subcutaneously established breast cancer model.

The results are shown in FIG. 7: although at the 2 week time point, only a small percentage of cells initially appear to show a shift in fluorescence, highly efficient gene transfer throughout the entire tumor is evidenced by FACS analysis of disaggregated tumor cells 4-6 weeks after injection of the initial inoculum. Intact, full-length genomic bands were detected in Southern blots of proviral DNA isolated from individual tumors at the 4 and 6 week time points. This indicates that the RCR vector was capable of efficient replication and gene delivery in the context of solid tumors in vivo without deletions occurring during this time interval, and provides an illustrative example of the potential power of this strategy for cancer gene therapy, especially considering the extremely low MOI of the initial inoculum.

Example 10

IRES Sequence Variations

Figure 14:
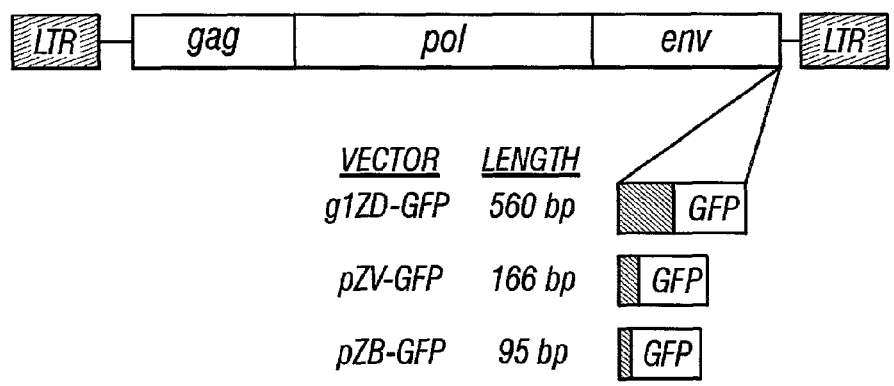
FIG. 14 shows the structure of RCR vectors with shorter IRES sequences.
Figure 15:
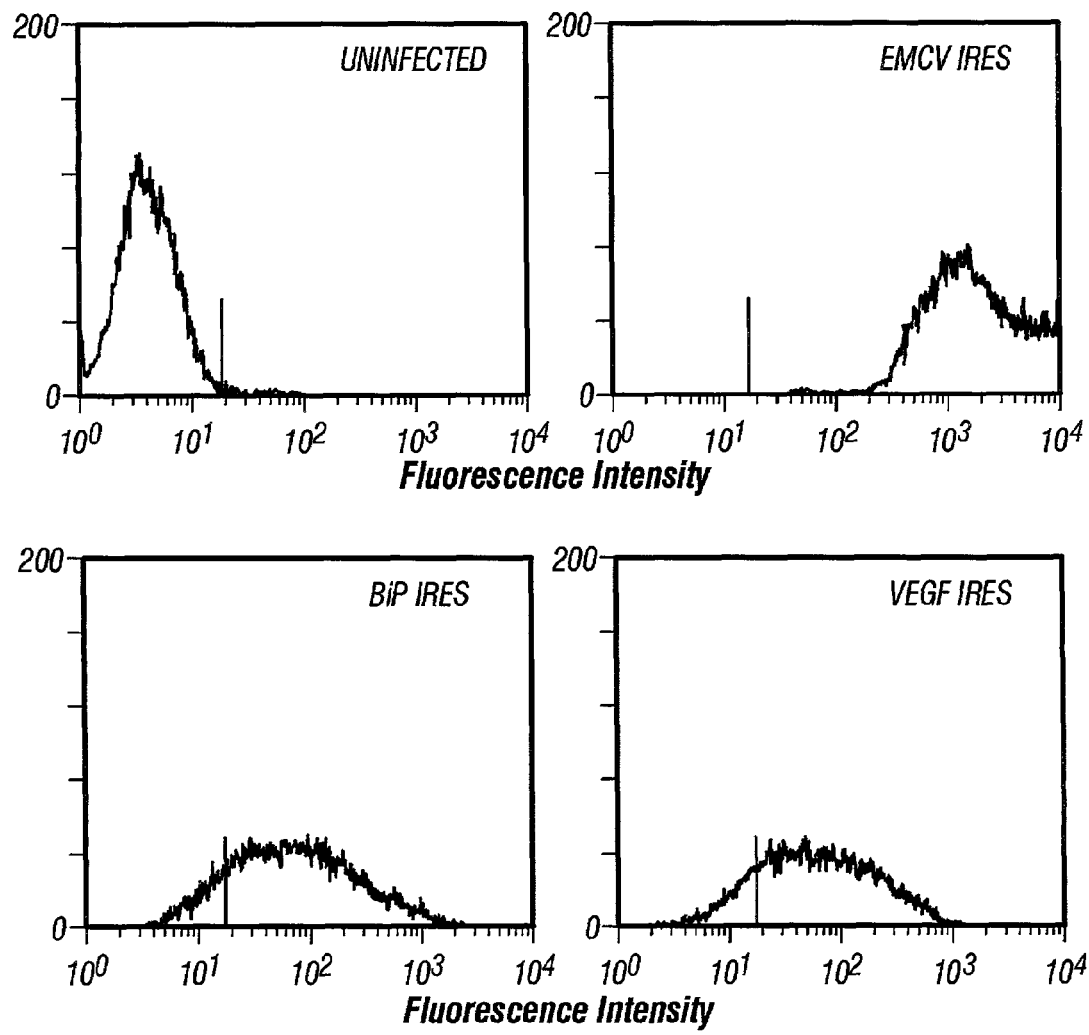
FIG. 15 shows a comparison of GFP expression levels in cells infected with vectors utilizing three different IRES sequences.
Figure 16A:
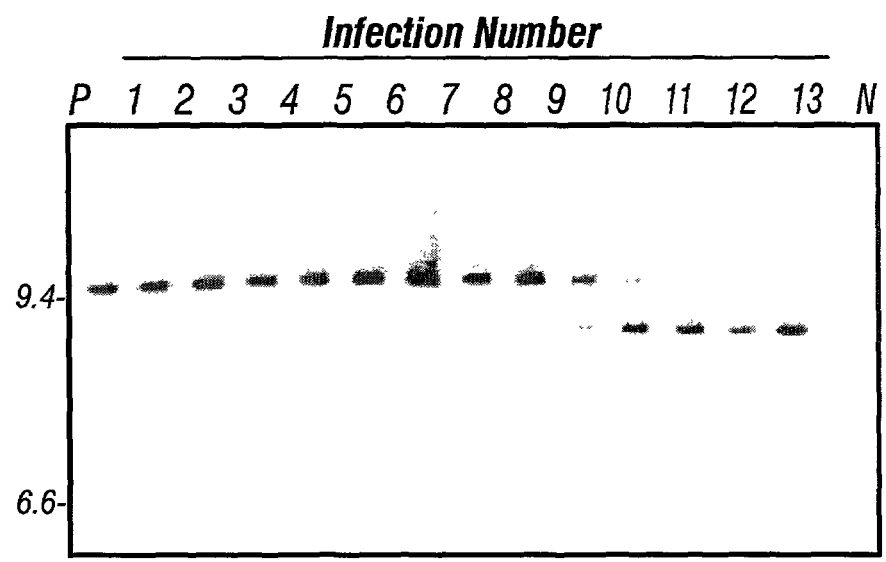
FIG. 16 is a Southern Blot analysis of unintegrated proviral DNA from cultured cells serially infected with ZB-GFP (A) or ZV-GFP (B). The probes used were for the LTR-gag region of Mo-MLV.
Figure 16B:
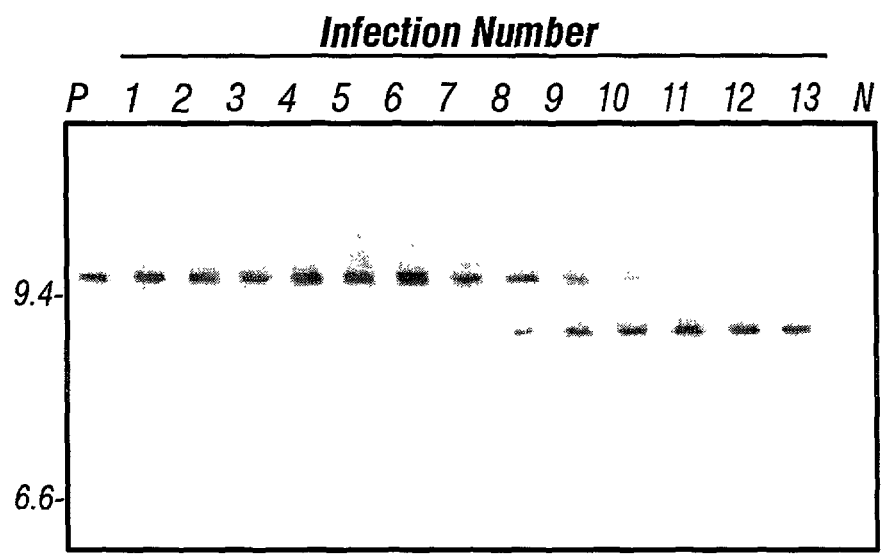

As described above, vectors were constructed varying the size of the viral genome. By using IRES sequences shorter than the EMCV IRES present in the constructs above, it may be possible to insert transgenes larger than GFP or large cell type-specific targeting sequences. Two new vectors were constructed using IRES sequences from the BiP (Yang and Sarnow, 1997) and VEGF (Stein et al., 1998) genes (FIG. 14). The BiP IRES-containing vector, ZB-GFP, and the VEGF IRES-containing vector, ZV-GFP, are 450 bp and 380 bp shorter than g1ZD-GFP, respectively. Infection of NIH3T3 cells by the vectors demonstrated that both efficiently transduce cells and express GFP, although transgene expression levels are somewhat lower than with g1ZD-GFP (FIG. 15). The ability of ZB-GFP and ZV-GFP to retain their IRES-GFP sequences through vector spread was determined by conducting serial infections of NIH3T3 cells with the vectors. Proviral (Hirt) DNA was prepared from 13 serially infected NIH3T3 populations and was subjected to Southern analysis using a probe for the LTR-gag region of Mo-MLV. FIG. 16 shows that the IRES-GFP sequences of both of the new vectors were retained for approximately the same number of serial infections as that of ZAPd-GFP. This indicated that a reduction in the size of the IRES in these vectors does not significantly alter vector stability, but may allow the insertion of transgenes larger than GFP.

Example 11

Figure 17:
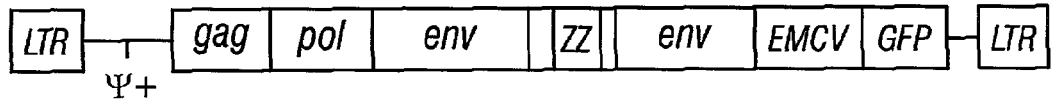
FIG. 17 is a schematic of Z-domain targeted RCR vectors. Both vectors contain 2 tandem copies of the Z domain of protein A within the PRR of the envelope gene. In ZE-GFP, GFP translation is driven by the EMCV IRES, and in ZV-A-GFP by the VEGF IRES.
Figure 17:
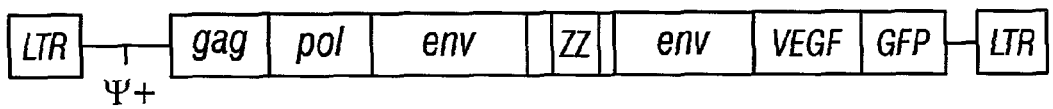
Figure 18:
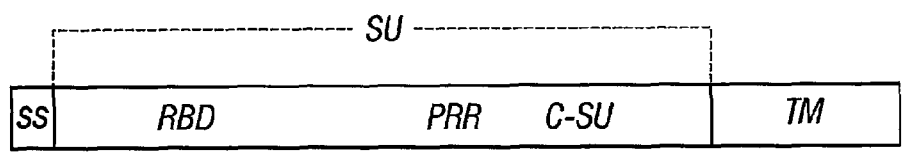
FIG. 18 is a schematic showing the envelope structure of RCR vectors containing anti-HER2 scFv. ss: signal sequence; SU: surface protein; RBD: receptor-binding domain; PRR: proline-rich region; C-SU: C-terminus of SU; TM: transmembrane protein; spacer: a synthetic 6 amino acid spacer.
Figure 18:
Figure 18:

RCR Vectors Targeted to Breast Tumor Cells Using Two Types of Modification to the Envelope Protein In order to obtain RCR vectors targeted to breast tumor cells, vectors were constructed containing modifications in the envelope gene that would allow specific binding of vector particles to proteins expressed on the surface of breast tumor cells. Two approaches in targeting the vectors were used. The first approach involves insertion of sequences encoding the IgG-binding domain ("Z domain," Nilsson et al., 1987) of the *S. aureus* protein A into the proline-rich region (PRR, or "hinge") of the envelope gene (FIG. 17). The presence of the Z domain on the vector surface would allow the binding of tumor-specific antibodies to the vector and would therefore presumably allow specific binding of the vector to tumor cells via the antibody. The second approach involves the replacement of the wild type receptor binding domain (RBD) of the envelope with sequences encoding a single-chain antibody (scFv) against HER2 (kindly provided by Drs. Michael Press and Jinha Park), (FIG. 18). This modification is expected to ablate binding of the vector to its normal receptor while allowing direct binding to HER2-expressing tumor cells.

Although the invention has been described with reference to the presently preferred embodiment, it should be understood that various modifications can be made without departing from the spirit of the invention. Accordingly, the invention is limited only by the following claims.

What is claimed is:

1. A method of treating a mammalian subject having a cell proliferative disorder comprising:
   a) contacting the mammalian subject with a therapeutically effective amount of a recombinant replication competent mammalian oncoretrovirus that infects mammalian cells, comprising:
      a retroviral GAG protein;
      a retroviral POL protein;
      a retroviral envelope;
      a mammalian oncoretroviral polynucleotide sequence comprising Long Terminal Repeat (LTR) sequences at the 5' and 3' ends of the mammalian oncoretroviral polynucleotide sequence;
      a cassette comprising an internal ribosome entry site (IRES) operably linked to heterologous nucleic acid sequence, wherein the cassette is positioned 5' to the 3' LTR, and just downstream and 3' to the sequence encoding the retroviral envelope, wherein the heterologous nucleic acid encodes a suicide gene and wherein the heterologous nucleic acid is expressed; and
      cis-acting nucleic acid sequences for reverse transcription, packaging and integration in a target cell; and
   b) contacting the mammalian subject with a prodrug which is activated by the expression of the suicide gene;
   wherein the cell proliferative disorder is a neoplastic disorder or associated with an overgrowth of connective tissue.

2. The method of claim 1, wherein the mammalian subject is a human.

3. The method of claim 1, wherein the contacting is by in vivo administration of the retrovirus.

4. The method of claim 3, wherein the in vivo administration is by systemic, local, or topical administration.

5. The method of claim 1, wherein the contacting is by ex vivo administration of the retrovirus.

6. The method of claim 1, wherein the mammalian oncoretroviral polynucleotide sequence is selected from the group consisting of murine leukemia virus (MLV), Moloney murine leukemia virus (MoMLV), Gibbon ape leukemia virus (GALV) and Human Foamy Virus (HFV).

7. The method of claim 6, wherein the MLV is an amphotropic MoMLV.

8. The method of claim 1, wherein the cell proliferative disorder is selected from the group consisting of lung cancer, colon-rectum cancer, breast cancer, prostate cancer, urinary tract cancer, uterine cancer, brain cancer lymphoma, head and neck cancer, pancreatic cancer, melanoma, stomach cancer and ovarian cancer.

9. The method of claim 1, wherein the LTR of the retrovirus comprises a tissue-specific promoter sequence.

10. The method of claim 9, wherein the tissue-specific promoter sequence is a probasin promoter sequence or a growth regulatory gene promoter sequence.

11. The method of claim 1 wherein the retroviral envelope comprise a chimeric protein.

12. The method of claim 11, wherein the chimeric protein comprises an ENV protein and a targeting polypeptide.

13. The method of claim 12, wherein the ENV protein is selected from the group consisting of murine leukemia virus (MLV) ENV protein and vesicular stomatitis virus (VSV) ENV protein.

14. The method of claim 12, wherein the targeting polypeptide is an antibody, a receptor, or a receptor ligand.

15. A method of treating a mammalian subject having a cell proliferative disorder comprising:
a) contacting the mammalian subject with a therapeutically effective amount of a recombinant replication competent mammalian oncoretroviral polynucleotide, comprising:
a polynucleotide sequence encoding a retroviral GAG protein;
a polynucleotide sequence encoding a retroviral POL protein;
a polynucleotide sequence encoding a retroviral envelope;
a mammalian oncoretroviral polynucleotide sequence comprising Long Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid is expressed; and
cis-acting nucleic acid sequences for reverse transcription, packaging and integration in a target cell; and
b) contacting the mammalian subject with a prodrug which is activated by the expression of the suicide gene;
wherein the cell proliferative disorder is a neoplastic disorder or associated with an overgrowth of connective tissue.

16. The method of claim 15, wherein the polynucleotide sequence encoding a retroviral envelope encodes a chimeric protein.

17. The method of claim 16, wherein the chimetic protein comprises an ENV protein and a targeting polypeptide.

18. The method of claim 17, wherein the targeting polypeptide is an antibody, a receptor, or a receptor ligand.

19. The method of claim 15, wherein GAG, POL and retroviral envelope polynucleotide sequences are from murine leukemia virus (MLV) or Moloney murine leukemia virus (MoMLV).

20. The method of claim 19, wherein the MoMLV is an amphotropic MoMLV.

21. The method of claim 17, wherein the ENV protein is an ecotropic protein.

22. The method of claim 17, wherein the ENV protein is selected from the group consisting of murine leukemia virus (MoMLV) ENV protein and vesicular stomatitis virus (VSV) ENV protein.

23. The method of claim 8, wherein the cell proliferative disorder is melanoma.

24. The method of claim 18, wherein the polynucleotide sequence is contained in a viral particle.

25. The method of claim 15, wherein the polynucleotide sequence is contained in a pharmaceutically acceptable carrier.

26. A method of treating a mammalian subject having a cell proliferative disorder comprising:
a) contacting the mammalian subject with a therapeutically effective amount of a recombinant replication competent murine leukemia virus (MLV) that infects mammalian cells, comprising:
an MLV GAG protein;
an MLV POL protein;
an MLV envelope;
an MLV polynucleotide sequence comprising Long-Terminal Repeat (LTR) sequences at the 5' and the 3' ends of the MLV polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid sequence is expressed; and
cis-acting nucleic acid sequences for reverse transcription, packaging and integration in a target cell; and
b) contacting the mammalian subject with a prodrug which is activated by the expression of the suicide gene;
wherein the cell proliferative disorder is a neoplastic disorder or associated with an overgrowth of connective tissue.

27. A method of treating a mammalian subject having a cell proliferative disorder comprising:
a) contacting the mammalian subject with a therapeutically effective amount of a recombinant replication competent mammalian oncoretrovirus that infects mammalian cells comprising:
a retroviral GAG protein;
a retroviral POL protein;
a retroviral envelope comprising a chimeric env protein comprising a targeting ligand;
a mammalian oncoretroviral polynucleotide sequence comprising Long Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid sequence is expressed; and
cis-acting nucleic acid sequences for reverse transcription, packaging and integration in a target cell; and
b) contacting the mammalian subject with a prodrug which is activated by the expression of the suicide gene;
wherein the cell proliferative disorder is a neoplastic disorder or associated with an overgrowth of connective tissue.

28. A method of treating a mammalian subject having a cell proliferative disorder comprising;
   a) contacting the mammalian subject with a therapeutically effective amount of a recombinant replication competent mammalian oncoretroviral polynucleotide, comprising:
      a polynucleotide sequence encoding a retroviral GAG protein;
      a polynucleotide sequence encoding a retroviral POL protein;
      a polynucleotide sequence encoding a retroviral envelope; wherein said envelope comprises a chimeric env protein comprising a targeting ligand;
      a mammalian oncoretroviral polynucleotide sequence comprising Long Terminal Repeat (LTR) sequences at the 5' and 3' ends of the mammalian oncoretroviral polynucleotide sequence;
      a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid sequence is expressed; and
      cis-acting nucleic acid sequences involved in reverse transcription, packaging and integration in a target cell; and
   b) contacting the mammalian subject with a prodrug which is activated by the expression of the suicide gene;
   wherein the cell proliferative disorder is a neoplastic disorder or associated with an overgrowth of connective tissue.

29. A method of treating a glioblastoma in a mammalian subject comprising:
   a) administering a therapeutically effective amount of a recombinant replication competent mammalian oncoretrovirus that infects mammalian cells to the mammalian subject, wherein the mammalian oncoretrovirus comprising:
      a retroviral GAG protein;
      a retroviral POL protein;
      a retroviral envelope;
      a mammalian oncoretroviral polynucleotide sequence comprising Long-Terminal Repeat (LTR) sequences at the 5' and 3' ends of the retroviral polynucleotide sequence;
      a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid sequence is expressed; and
      cis-acting nucleic acid sequences for reverse transcription, packaging and integration in a target cell; and
   b) administering a prodrug which is activated by the expression of the suicide gene to the mammalian subject.

30. The method of claim 29, wherein the LTR comprises a tissue specific promoter sequence.

31. A method of treating glioblastoma in mammalian subject comprising:
   a) administering a therapeutically effective amount of a recombinant mammalian oncoretroviral polynucleotide of the mammalian subject, wherein the recombinant mammalian retroviral polynucleotide comprises:
      a polynucleotide sequence encoding a encoding GAG protein;
      a polynucleotide sequence encoding a encoding POL protein;
      a polynucleotide sequence encoding a retroviral envelope;
      a mammalian oncoretroviral polynucleotide sequence comprising Long-Terminal Repeat (LTR) sequences at the 5' and 3' ends of the mammalian oncoretroviral polynucleotide sequence;
      a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the heterologous nucleic acid is expressed; and
      cis-acting nucleic acid sequences for reverse transcription, packaging and integration in a target cell; and
   b) administering a prodrug which is activated by the expression of the suicide gene to the mammalian subject.

32. The method of claim 31, wherein the LTR comprises a tissue specific promoter sequence.

33. A method of treating glioblastoma in a mammalian subject comprising:
   a) administering a therapeutically effective amount of a recombinant replication competent murine leukemia virus (MLV) to the mammalian subject, wherein the recombinant replication competent MLV comprises:
      an MLV GAG protein;
      an MLV POL protein;
      an MLV envelope;
      an MLV polynucleotide sequence comprising Long-Terminal Repeat (LTR) sequences at the 5' and the 3' ends of the MLV polynucleotide sequence;
      a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the suicide gene is expressed; and
      cis-acting nucleic acid sequences for reverse transcription, packaging and integration in a target cell; and
   b) administering a prodrug which is activated by the expression of the suicide gene to the mammalian subject.

34. The method of claim 33, wherein the LTR comprises a tissue specific promoter sequence.

35. A method of treating glioblastoma in a mammalian subject comprising:
   a) administering a therapeutically effective amount of a recombinant replication competent mammalian oncoretrovirus that infects mammalian cells to the mammalian subject, wherein the recombiant replication competent mammalian oncoretrovirus comprises:
      a retroviral GAG protein;
      a retroviral POL protein;
      a retroviral envelope comprising a chimeric env protein comprising a targeting ligand;

a mammalian oncoretroviral polynucleotide sequence comprising Long-Terminal Repeat (LTR) sequences at the 5' and 3' ends of the mammalian oncoretroviral polynucleotide sequence;

a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the suicide gene is expressed; and cis-acting nucleic acid sequences for reverse transcription, packaging and integration in a target cell; and b) administering a prodrug which is activated by the expression of the suicide gene to the mammalian subject.

36. The method of claim 35, wherein the LTR comprises a tissue specific promoter sequence.

37. A method of treating glioblastoma in a mammalian subject comprising:
a) administering a therapeutically effective amount of a recombinant mammalian oncoretroviral polynucleotide to the mammalian subject wherein the recombinant mammalian oncoretrobiral polynucleotide comprises:
a polynucleotide sequence encoding a GAG protein;
a polynucleotide sequence encoding a POL protein;
a polynucleotide sequence encoding a retroviral envelope, wherein said envelope comprises a chimeric env protein comprising a targeting ligand;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the suicide gene is expressed; and
cis-acting nucleic acid sequences for reverse transcription, packaging and integration in a target cell; and
b) administering a prodrug which is activated by the expression of the suicide gene to the mammalian subject.

38. The method of claim 37, wherein the LTR comprises a tissue specific promoter sequence.

39. A method of treating a mammalian subject having a cell proliferative disorder comprising:
contacting the mammalian subject with a therapeutically effective amount of a recombinant replication competent mammalian oncoretrovirus that infects mammalian cells comprising:
a retroviral GAG protein;
a retroviral POL protein;
a retroviral envelope;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a cytokine and the cytokine is expressed; and
cis-acting nucleic acid sequences for reverse transcription, packaging and integration in a target cell; and
wherein the cell proliferative disorder is a neoplastic disorder or associated with an overgrowth of connective tissue.

40. The method of claim 39, wherein the cell proliferated disorder is selected from the group consisting of lung cancer, colon-rectum cancer, breast cancer, prostate cancer, urinary tract cancer, uterine cancer, brain cancer, lymphoma, head and neck cancer, pancreatic cancer, melanoma, stomach cancer and ovarian cancer.

41. A method of treating a mammalian subject having a cell proliferative disorder comprising:
contacting the mammalian subject with a therapeutically effective amount of a recombinant replication competent mammalian oncoretroviral polynucleotide, comprising:
a polynucleotide sequence encoding retroviral GAG protein;
a polynucleotide sequence encoding retroviral POL protein;
a polynucleotide sequence encoding retroviral envelope;
a mammalian oncoretroviral polynucleotide sequence comprising Long Terminal Repeat (LTR) sequences at the 5' and 3' ends of the mammalian oncoretroviral polynucleotide sequence;
a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein the heterologous nucleic acid encodes a cytokine and wherein the cytokine is expressed; and
cis-acting nucleic acid sequences or reverse transcription, packaging and integration n a target cell, wherein the cell proliferative disorder is a neoplastic disorder or associated with an overgrowth of connective tissue.

42. The method of claim 41, wherein the cell proliferative disorder is melanoma.

43. A method of treating a mammalian subject having a cell proliferative disorder comprising:
contacting the mammalian subject with a therapeutically effective amount of a recombinant replication competent murine leukemia virus (MLV), comprising:
an MLV GAG protein;
an MLV POL protein;
an MLV envelope;
an MLV polynucleotide sequence comprising Long-Terminal Repeat (LTR) sequences at the 5' and 3' ends of the MLV polynucleotide sequence;
a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein cytokine is expressed; and
cis-acting nucleic acid sequences for reverse transcription, packaging and integration in a target cell, wherein the cell proliferative disorder is a neoplastic disorder or associated with an overgrowth of connective tissue.

44. A method of treating a mammalian subject having a cell proliferative disorder comprising:
contacting the mammalian subject with a therapeutically effective amount of a recombinant replication competent mammalian oncoretrovirus that infects mammalian cells comprising:

a retroviral GAG protein;
a retroviral POL protein;
a retroviral envelope comprising a chimereic env protein comprising a targeting ligand;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a cytokine and wherein the cytokine is expressed; and
cis-acting nucleic acid sequences for reverse transcription, packaging and integration in a target cell, wherein the cell proliferative disorder is a neoplastic disorder or associated with an overgrowth of connective tissue.

45. A method of treating a mammalian subject having a cell proliferative disorder comprising:
contacting the mammalian subject with a therapeutically effective amount of a recombinant replication competent mammalian oncoretroviral polynucleotide, comprising:
a polynucleotide sequence encoding retroviral GAG protein;
a polynucleotide sequence encoding retroviral POL protein;
a polynucleotide sequence encoding retroviral envelope, wherein said envelope comprises a chimeric env protein comprising a targeting ligand;
a mammalian oncoretroviral polynucleotide sequence comprising Long Terminal Repeat (LTR) sequences at the 5' and 3' ends of the mammalian oncoretroviral polynucleotide sequence;
a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein the heterologous nucleic acid encodes a cytokine and wherein the cytokine is expressed; and
cis-acting nucleic acid sequences or reverse transcription, packaging and integration in a target cell, wherein the cell proliferative disorder is a neoplastic disorder or associated with an overgrowth of connective tissue.

46. A method of treating gliblastoma in a mammalian subject comprising:
administering a therapeutically effective amount of a recombiant replication competent mammalian oncoretrovirus that infects mammalian cells to the mammalian subject, wherein the mammalian oncoretrovirus comprises:
a retroviral GAG protein;
a retroviral POL protein;
a retroviral envelope;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a cytokine and wherein the cytokine is expressed; and
cis-acting nucleic acid sequences for reverse transcription, packaging and integration in a target cell.

47. The method of claim 46,, wherein the LTR comprises a tissue specific promoter sequence.

48. A method of treating gliblastoma in a mammalian subject comprising:
administering a therapeutically effective amount of a recombiant mammalian oncoretroviral polynucleotide to the mammalian subject, wherein the recombinant mammalian oncoretroviral polynucleotide comprises:
a polynucleotide sequence encoding GAG protein;
a polynucleotide sequence encoding POL protein;
a polynucleotide sequence encoding retroviral envelope;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein the heterologous nucleic acid encodes a cytokine and wherein the cytokine is expressed; and
cis-acting nucleic acid sequences or reverse transcription, packaging and integration in a target cell.

49. The method of claim 48, wherein the LTR comprises a tissue specific promoter sequence.

50. A method of treating gliblastoma in a mammalian subject comprising:
administering a therapeutically effective amount of a recombinant replication competent murine leukemia a virus (MLV) to the mammalian subject, wherein the recombinant replication competent MLV comprises:
a MLV GAG protein;
a MLV POL protein;
an MLV envelope;
a MLV polynucleotide sequence comprising Long-Terminal Repeat (LTR) sequences at the 5' and 3' ends of the MLV polynucleotide sequence; a cassette comprising an internal ribosome entry site (IRES) operably linked to heterologous nucleic acid sequence, wherein the cassette is positioned 5'to the 3' LTR, and just downstream and 3' to the sequence encoding the retroviral envelope, wherein the heterologous nucleic acid encodes a cytokine and wherein the cytokine is expressed; and
cis-acting nucleic acid sequences for reverse transcription, packaging and integration in a target cell.

51. The method of claim 50, wherein the LTR comprises a tissue specific promoter sequences.

52. A method of treating gliblastoma in a mammalian subject comprising:
administering a therapeutically effective amount of a recombinant replication competent mammalian oncoretrovirus that infects mammalian cells to the mammalian subject, wherein the recombinant replication competent mammalian oncoretrovirus comprises:
a retroviral GAG protein;
a retroviral POL protein;
an retroviral envelope comprising a chimeric env protein comprising a targeting ligand;

a mammalian oncoretroviral polynucleotide sequence comprising Long Terminal Repeat (LTR) sequences at the 5' and 3' ends of the MLV polynucleotide sequence;

a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein the heterologous nucleic acid encodes a cytokine and wherein the cytokine is expressed; and cis-acting nucleic acid sequences or reverse transcription, packaging and integration in a target cell.

53. The method of claim 52, wherein the LTR comprises a tissue specific promoter sequence.

54. A method of treating glioblastoma in a mammalian subject comprising:

administering a therapeutically effective amount of a recombiant mammalian oncoretroviral polynucleotide to the mammalian subject, wherein the recombinant mammalian oncoretroviral polynucleotide comprises:
a polynucleotide sequence encoding GAG protein;
a polynucleotide sequence encoding POL protein;
a polynucleotide sequence encoding retroviral envelope, wherein said envelope comprises a chimeric env protein comprising a targeting ligand;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to a heterologous nucleic acid sequence, wherein the cassette is positioned 5' to the 3' LTR, and just downstream and 3' to the sequence encoding the retroviral envelope, wherein the heterologous nucleic acid encodes a cytokine and wherein the cytokine is expressed; and
cis-acting nucleic acid sequences or reverse transcription, packaging and integration in a target cell.

55. The method of claim 54, wherein the LTR comprises a tissue specific promoter sequence.

56. The method of claim 39, wherein the mammalian oncoretrovirus is selected from the group consisting of murine leukemia virus (MLV), Moloney murine leukemia virus (MoMLV), and Gibbon ape leukemia virus(GALV).

57. The method of claim 39, wherein the cytokine is selected from the group consisting of interleukins 1 through 12, interferon, tumor necrosis facto (TNF), and granulocyte-macrophage-colony stimulating factor (Gm-CSF).

58. The method of claim 57, wherein the cytokine is interferon.

59. The method of claim 58, wherein the interferon is gamma interferon.

60. A method of treating a mammalian subject having a cell proliferative disorder comprising:

contacting the mammalian subject, with therapeutically effective amount of a recombinant replication competent mammalian oncoretrovirus that infects mammalian cells comprises:
a retroviral GAG protein;
a retroviral POL protein;
a retroviral or non-retroviral envelope;
a mammalian oncoretroviral polynucleotide sequence comprising Long-Terminal Repeat (LTR) sequences at the 5' and 3' ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a cytokine and wherein the cytokine is expressed; and
cis-acting nucleic acid sequences for reverse transcription, packaging and integration in a target cell.

61. The method of claim 60, wherein the non-retroviral envelope is derived from VSV, CMV or influenza virus.

62. A method of treating a mammalian subject having a cell proliferative disorder comprising:

contacting the mammalian subject with therapeutically effective amount of a recombinant replication competent mammalian oncoretrovirus that infects mammalian cells comprises:
a retroviral GAG protein;
a retroviral POL protein;
a retroviral envelope;
a mammalian oncoretroviral polynucleotide sequence comprising Long-Terminal Repeat (LTR) sequences at the 5'and 3'ends of the mammalian oncoretroviral polynucleotide sequence;
a cassette comprising an internal ribosome entry site (IRES) operably linked to heterologous nucleic acid sequence, wherein the cassette is positioned 5' and the 3' LTR, and just downstream and 3' to the sequence encoding the retroviral envelope, wherein the heterologous nucleic acid encodes a suicide gene and wherein the suicide gene is expressed; and
cis-acting nucleic acid sequences for reverse transcription, packaging and integration in a target cell.

* * * * *